(12) United States Patent
Zhu et al.

(10) Patent No.: US 10,736,845 B2
(45) Date of Patent: Aug. 11, 2020

(54) DUAL LOADED LIPOSOMAL PHARMACEUTICAL FORMULATIONS

(71) Applicant: Cureport, Inc., Worcester, MA (US)

(72) Inventors: De-Min Zhu, Westborough, MA (US); Guoqiang Chen, Shrewsbury, MA (US)

(73) Assignee: Cureport Inc., Worchester, MA (US)

( * ) Notice: Subject to any disclaimer, the term of this patent is extended or adjusted under 35 U.S.C. 154(b) by 0 days.

(21) Appl. No.: 15/059,943

(22) Filed: Mar. 3, 2016

(65) Prior Publication Data

US 2016/0256387 A1    Sep. 8, 2016

Related U.S. Application Data

(60) Provisional application No. 62/127,479, filed on Mar. 3, 2015.

(51) Int. Cl.
| | | |
|---|---|---|
| *A61K 9/127* | (2006.01) | |
| *A61K 9/00* | (2006.01) | |
| *A61K 31/337* | (2006.01) | |
| *A61K 31/704* | (2006.01) | |

(52) U.S. Cl.
CPC ............ *A61K 9/127* (2013.01); *A61K 9/0019* (2013.01); *A61K 9/1271* (2013.01); *A61K 9/1272* (2013.01); *A61K 9/1278* (2013.01); *A61K 31/337* (2013.01); *A61K 31/704* (2013.01)

(58) Field of Classification Search
None
See application file for complete search history.

(56) References Cited

U.S. PATENT DOCUMENTS

| | | | |
|---|---|---|---|
| 4,898,735 A | * | 2/1990 | Barenholz .............. A61K 9/127 264/4.1 |
| 5,013,556 A | * | 5/1991 | Woodle ................ A61K 9/1271 264/4.3 |
| 5,264,618 A | * | 11/1993 | Felgner ................ A61K 9/0014 530/323 |
| 6,676,941 B2 | | 1/2004 | Thorpe et al. |
| 7,153,490 B2 | | 12/2006 | Parente Duena et al. |
| 7,511,016 B2 | | 3/2009 | Reutelingsperger |
| 7,850,990 B2 | | 12/2010 | Tardi et al. |
| 8,246,983 B2 | | 8/2012 | O'Halloran et al. |
| 8,293,240 B2 | | 10/2012 | Newell et al. |
| 8,404,681 B2 | | 3/2013 | Halbrook et al. |
| 8,476,242 B2 | | 7/2013 | Mon |
| 8,591,942 B2 | | 11/2013 | Javeri et al. |
| 8,747,869 B2 | | 6/2014 | Irvine et al. |
| 8,747,891 B2 | | 6/2014 | Kester et al. |
| 2004/0265367 A1 | | 12/2004 | Thorpe et al. |
| 2005/0202076 A1 | | 9/2005 | Mundus et al. |
| 2006/0165744 A1 | | 7/2006 | Jamil et al. |
| 2006/0228694 A1 | | 10/2006 | Janoff et al. |
| 2007/0071804 A1 | * | 3/2007 | Balu-Iyer .............. A61K 38/208 424/450 |
| 2008/0075762 A1 | | 3/2008 | Tardi et al. |
| 2008/0107721 A1 | | 5/2008 | Lewis et al. |
| 2008/0286351 A1 | | 11/2008 | Ahmad et al. |
| 2008/0311182 A1 | | 12/2008 | Ferrari et al. |
| 2009/0053302 A1 | | 2/2009 | Boulikas |
| 2009/0098212 A1 | | 4/2009 | Fossheim et al. |
| 2009/0162425 A1 | | 6/2009 | Divi et al. |
| 2010/0034749 A1 | | 2/2010 | Schulze et al. |
| 2010/0099737 A1 | | 4/2010 | Krystal et al. |
| 2010/0104629 A1 | | 4/2010 | Dande et al. |
| 2010/0166872 A1 | | 7/2010 | Singh et al. |
| 2010/0297023 A1 | | 11/2010 | Miller et al. |
| 2010/0331819 A1 | | 12/2010 | Hossainy et al. |
| 2011/0070294 A1 | | 3/2011 | Javeri et al. |
| 2011/0177156 A1 | | 7/2011 | Szoka, Jr. et al. |
| 2011/0237686 A1 | | 9/2011 | Ng et al. |
| 2011/0250259 A1 | | 10/2011 | Buckman |
| 2011/0313017 A1 | | 12/2011 | Heyes |
| 2012/0058178 A1 | | 3/2012 | Kikuchi et al. |
| 2012/0082717 A1 | | 4/2012 | Char et al. |
| 2012/0128757 A1 | | 5/2012 | Kikuchi et al. |
| 2012/0141578 A1 | | 6/2012 | Robertson et al. |

(Continued)

FOREIGN PATENT DOCUMENTS

| | | |
|---|---|---|
| CN | 102091036 | 6/2011 |
| CN | 102225054 | 10/2011 |

(Continued)

OTHER PUBLICATIONS

U.S. Appl. No. 14/209,187, filed Mar. 13, 2014, Methods and Devices for Preparation of Lipid Nanoparticles.
Alexopoulos, A., et al., Phase II study of pegylated liposomal doxorubicin (Caelyx) and docetaxel as first-line treatment in metastatic breast cancer. Ann Oncol. Jun. 2004;15(6):891-5.
De La Flouchardiere, C., et al., Docetaxel and pegylated liposomal doxorubicin combination as first-line therapy for metastatic breast cancer patients: results of the phase II GINECO trial CAPYTTOLE. Ann Oncol. Dec. 2009;20(12):1959-63. doi: 10.1093/annonc/mdp231. Epub Jun. 25, 2009.

(Continued)

*Primary Examiner* — Celeste A Roney

(74) *Attorney, Agent, or Firm* — Fish & Richardson P.C.

(57) ABSTRACT

A pharmaceutical composition can include a plurality of liposomes comprising docetaxel and doxorubicin. In various embodiments, a liposome can include (i) an active pharmaceutical ingredient (API) comprising docetaxel and doxorubicin; (ii) a lipid layer comprising an unsaturated phospholipid, a cholesterol, a cationic lipid, and preferably a pegylated phospholipid; and (iii) an aqueous interior, wherein the docetaxel is in the lipid layer and the doxorubicin is crystallized in the aqueous interior. The liposomes can be used to treat a subject, for example, a human subject having cancer. The cancer can be, for example, a lung cancer, preferably non-small cell lung cancer (NSCLC), colon cancer, breast cancer, or liver cancer.

20 Claims, 8 Drawing Sheets

(56) References Cited

U.S. PATENT DOCUMENTS

| | | | |
|---|---|---|---|
| 2012/0225115 A1 | 9/2012 | Au et al. | |
| 2012/0294930 A1 | 11/2012 | Ren et al. | |
| 2012/0310142 A1 | 12/2012 | Hossainy et al. | |
| 2013/0102898 A1 | 4/2013 | Kim et al. | |
| 2013/0102993 A1 | 4/2013 | Kim et al. | |
| 2013/0115273 A1 | 5/2013 | Yang et al. | |
| 2013/0122056 A1 | 5/2013 | Zhang et al. | |
| 2013/0129812 A1 | 5/2013 | Ozpolat et al. | |
| 2013/0315986 A1 | 11/2013 | Cheong et al. | |
| 2013/0337066 A1 | 12/2013 | Zhang et al. | |
| 2013/0345286 A1 | 12/2013 | Gollob et al. | |
| 2014/0011759 A1 | 1/2014 | Yaffe et al. | |
| 2014/0024699 A1 | 1/2014 | Kaelin, Jr. et al. | |
| 2014/0187501 A1 | 7/2014 | Bilodeau et al. | |
| 2014/0271821 A1* | 9/2014 | McGhee | A61K 9/127 424/450 |
| 2014/0348900 A1 | 11/2014 | Zhu | |
| 2015/0299241 A1* | 10/2015 | Chen | C07H 15/252 536/6.4 |
| 2016/0256389 A1 | 9/2016 | Zhu et al. | |

FOREIGN PATENT DOCUMENTS

| | | | |
|---|---|---|---|
| CN | 103622912 | * | 3/2012 |
| CN | 102935068 | | 2/2013 |
| CN | 103087124 | | 5/2013 |
| EP | 1 325 739 A1 | | 7/2003 |
| EP | 1 214 078 B1 | | 11/2004 |
| EP | 1 537 858 A1 | | 6/2005 |
| EP | 2 215 107 B1 | | 10/2012 |
| EP | 1 915 374 B1 | | 4/2014 |
| WO | WO-02-072068 | * | 9/2002 |
| WO | 02/085311 A2 | | 10/2002 |
| WO | 2005/053642 A1 | | 6/2005 |
| WO | 2006/055697 A2 | | 5/2006 |
| WO | 2007/072221 A2 | | 6/2007 |
| WO | 2008/021908 A2 | | 2/2008 |
| WO | 2008/039188 A1 | | 4/2008 |
| WO | 2009/051712 A1 | | 4/2009 |
| WO | WO-2010-009186 | * | 1/2010 |
| WO | 2010/065329 A2 | | 6/2010 |
| WO | 2010/108934 A1 | | 9/2010 |
| WO | 2011/115684 A2 | | 9/2011 |
| WO | 2011/120023 A1 | | 9/2011 |
| WO | 2011/134675 A1 | | 11/2011 |
| WO | 2012/015901 A1 | | 2/2012 |
| WO | 2012/021383 A2 | | 2/2012 |
| WO | 2012/170284 A1 | | 12/2012 |
| WO | 2013/012891 A1 | | 1/2013 |
| WO | 2013/052167 A2 | | 4/2013 |
| WO | 2013/066440 A1 | | 5/2013 |
| WO | 2013/155341 A1 | | 10/2013 |
| WO | 2013/188763 A1 | | 12/2013 |
| WO | 2014/015027 A1 | | 1/2014 |
| WO | WO-2014-079300 | * | 2/2014 |
| WO | 2014/057432 A2 | | 4/2014 |
| WO | 2014/071406 A1 | | 5/2014 |
| WO | 2014/093631 A1 | | 6/2014 |

OTHER PUBLICATIONS

Livi, L., et al., Non-pegylated liposomal doxorubicin in combination with cyclophosphamide or docetaxel as first-line therapy in metastatic breast cancer: a retrospective analysis. Tumori. Jul.-Aug. 2009;95(4):422-6.

Sparano, J.A., et al., Phase I trial of pegylated liposomal doxorubicin and docetaxel in advanced breast cancer. J Clin Oncol. Jun. 15, 2001;19(12):3117-25.

Sparano, J.A., et al., Pegylated liposomal doxorubicin plus docetaxel significantly improves time to progression without additive cardiotoxicity compared with docetaxel monotherapy in patients with advanced breast cancer previously treated with neoadjuvant-adjuvant anthracycline therapy: results from a randomized phase III study. J Clin Oncol. Sep. 20, 2009;27(27):4522-9. doi: 10.1200/JCO.2008.20.5013. Epub Aug. 17, 2009.

Wolff, A.C., et al., Phase II trial of pegylated liposomal doxorubicin plus docetaxel with and without trastuzumab in metastatic breast cancer: Eastern Cooperative Oncology Group trial E3198. Breast Cancer Res Treat. May 2010;121(1):111-20. doi: 10.1007/s10549-010-0838-7. Epub Mar. 24, 2010.

International Search Report for Application No. PCT/US2016/020647, dated May 5, 2016. (12 pages).

International Search Report for Application No. PCT/US2016/020654, dated May 5, 2016. (11 pages).

Immordino, M.L., et al., Preparation, characterization, cytotoxicity and pharmacokinetics of liposomes containing docetaxel. J Control Release. Sep. 4, 2003;91(3):417-29.

Zhao, L., et al., Solid dispersion and effervescent techniques used to prepare docetaxel liposomes for lung-targeted delivery system: in vitro and in vivo evaluation. J Drug Target. Apr. 2011;19(3):171-8. doi: 10.3109/10611861003801859. Epub Apr. 30, 2010.

Budman et al. (2002). "In vitro search for synergy and antagonism: evaluation of docetaxel combinations in breast cancer cell lines," Breast Cancer Research and Treatment, v. 74, pp. 41-46.

Cresta, S. et al., "A randomized phase II study of combination, alternating and sequential regimens of doxorubicin and docetaxel as first-line chemotherapy for women with metastatic breast cancer," Annals of Oncol., 2004, v. 15, pp. 433-439.

Fritze et al. (2006). "Remote loading of doxorubicin into liposomes driven by a transmembrane phosphate gradient." Biochimica et Biophysica Acta, v. 1758, pp. 1633-1640.

Miller, K. D. et al., "Combination Versus Sequential Doxorubicin and Docetaxel as Primary Chemotherapy for Breast Cancer: A Randomized Pilot Trial of the Hoosier Oncology Group," J. Clin. Oncol., 1999, v. 17, pp. 3033-3037.

Nabholtz, J-M, et al., "Docetaxel and Doxorubicin Compared With Doxorubicin and Cyclophosphamide as First-Line Chemotherapy for Metastatic Breast Cancer: Results of a Randomized, Multicenter, Phase III Trial," J. Clin. Oncol., 2003, v. 21, pp. 968-975.

Von Minckwitz, G., et al., "Doxorubicin With Cyclophosphamide Followed by Docetaxel Every 21 Days Compared With Doxorubicin and Docetaxel Every 14 Days as Preoperative Treatment in Operable Breast Cancer: The GEPARDUO Study of the German Breast Group," J. Clin. Oncol., 2005, v. 23, pp. 2676-2685.

[No Author Listed] Prescribing Information, DOXIL, revised May 2007, Manuf. Ben Venue Laboratories, pp. 1-33.

[No Author Listed] Prescribing Information TAXOTERE, revised May 2010, Sanofi-Aventis U.S. LLC, pp. 1-62.

Deeken, J. F., et al., A phase I study of liposomal-encapsulated docetaxel (LE-DT) in patients with advanced solid tumor malignancies. Cancer Chemother Pharmacol. Mar. 2013;71(3):627-33. doi: 10.1007/s00280-012-2048-y. Epub Dec. 30, 2012.

Haran, G. et al., "Transmembrane ammonium sulfate gradients in liposomes produce efficient and stable entrapment of amphipathic weak bases," Biochim et Biophys Acta, 1993, v. 1151, pp. 201-215.

Lewrick, F. et al., "Remote Loading of Anthracyclines into Liposomes," in Methods in Molecular Biology, V. Weissig, ed.; 2010, v. 605, Chapter 9, pp. 139-145.

Abu Lila et al., "Targeting Anticancer Drugs to Tumor Vasculature Using Cationic Liposomes," Pharmaceutical Research, Mar. 2010, 27: 1171-1183.

European Search Report in Application No. 16759478.7, dated Oct. 10, 2018, 8 pages.

CN Office Action for Chinese Appln. No. 201680013636.7, dated Dec. 2, 2019, 18 pages (with English translation).

* cited by examiner

*BLOQ: Below Limit of Quantitation

DUAL LOADED LIPOSOMAL PHARMACEUTICAL FORMULATIONS

CROSS-REFERENCE TO RELATED APPLICATIONS

This application claims the benefit of U.S. Provisional Application No. 62/127,479, filed Mar. 3, 2015, which is hereby incorporated by reference in its entirety.

FIELD OF THE INVENTION

The present invention generally relates to liposomal pharmaceutical formulations and, in various embodiments, more specifically to liposomal pharmaceutical formulations including an active pharmaceutical ingredient with two components (e.g., a combination of docetaxel and doxorubicin).

BACKGROUND

Liposome technology has been utilized for drug delivery in clinical therapy and scientific research. To date, a handful of liposomal pharmaceutical formulations have been approved by the US Food and Drug Administration ("FDA"), and a number of new liposomal formulations are in clinical trials. However, the field of liposomal formulation is still evolving and each active pharmaceutical ingredient ("API") presents unique challenges.

One area where liposomal formulations can be applied is in cancer APIs. For example, liposomal formulations of doxorubicin are presently available under the trade names Doxil® and Myocet®. Doxil® is a pegylated (polyethylene glycol coated) liposome-encapsulated form of doxorubicin formerly made by Ben Venue Laboratories in the United States for Janssen Products, LP, a subsidiary of Johnson & Johnson. Myocet® is a non-pegylated liposomal doxorubicin made by Enzon Pharmaceuticals for Cephalon in Europe and for Sopherion Therapeutics in the United States and Canada. Myocet® is approved in Europe and Canada for treatment of metastatic breast cancer in combination with cyclophosphamide, but is not yet approved by the FDA for use in the United States.

Despite the handful of approved liposomal pharmaceutical formulations, the field is still limited by the unique challenges and unpredictability of each different API, as well as the currently available methods of making liposomal formulations, which present difficult problems associated with scalability, low reproducibility, and product heterogeneity. There exists a need for improved liposomal formulations for use in drug delivery.

SUMMARY OF THE INVENTION

In various aspects and embodiments, the invention provides a pharmaceutical composition including a plurality of liposomes comprising a first drug (e.g., docetaxel) and a second drug (e.g., doxorubicin). In various embodiments, a liposome can include (i) an active pharmaceutical ingredient (API) comprising a first drug (e.g., docetaxel) and a second drug (e.g., doxorubicin); (ii) a lipid layer comprising an unsaturated phospholipid, a cholesterol, and preferably a pegylated phospholipid; and (iii) an aqueous interior, wherein the first drug (e.g., docetaxel) is in the lipid layer and the second drug (e.g., doxorubicin) is crystallized in the aqueous interior. The liposomes can be used to treat a subject, for example, a human subject having cancer. The cancer can be, for example, a lung cancer, preferably non-small cell lung cancer (NSCLC); colon cancer; breast cancer; or liver cancer, preferably hepatocellular carcinoma (HCC).

The invention can provide for increased efficacy and/or decreased toxicity, for example relative to (i) other pharmaceutical compositions where one or both of the first drug (e.g., docetaxel) and the second drug (e.g., doxorubicin) are not in a liposomal formulation and/or (ii) other liposomal formulations. The invention can provide for targeted delivery, for example to the liver or avoiding the liver. The invention can mitigate undesired side effects, for example by providing for increased drug loading, thereby reducing the amount of liposomes needed to deliver a quantity of the first drug (e.g., docetaxel) and the second drug (e.g., doxorubicin).

The invention provides a liposome comprising: (i) an active pharmaceutical ingredient (API) comprising docetaxel and doxorubicin; (ii) a lipid layer comprising an unsaturated phospholipid, a cholesterol, and preferably a pegylated phospholipid; and (iii) an aqueous interior, wherein the docetaxel is in the lipid layer and the doxorubicin is crystallized in the aqueous interior.

The invention also provides a pharmaceutical composition comprising a plurality of liposomes according to any of the aspects or embodiments disclosed herein.

The invention also provides a method comprising administering the liposome according to any of the aspects or embodiments disclosed herein, or the pharmaceutical composition according to any of the aspects or embodiments disclosed herein, to a subject.

The invention also provides a method of treating a subject comprising administering an effective amount of the liposome according to any of the aspects or embodiments disclosed herein, or the pharmaceutical composition according to any of the aspects or embodiments disclosed herein, to a subject.

The invention also provides a method of making the liposome according to any of the aspects or embodiments disclosed herein, or the pharmaceutical composition according to any of the aspects or embodiments disclosed herein, comprising: (i) introducing a lipid solution of an unsaturated phospholipid, cholesterol, a first drug (e.g., docetaxel), and preferably a pegylated phospholipid in ethanol through a first or more inlet port of a manifold into a mixing chamber and an aqueous solution through a second or more inlet port of the manifold into the mixing chamber, the liposomes formed exit the mixing chamber through a third or more outlet port of the manifold, thereby making a plurality of liposomes; and (ii) incubating the plurality of liposomes in a second drug (e.g., doxorubicin) solution.

In various embodiments, the lipid layer consists essentially of the unsaturated phospholipid and cholesterol.

In various embodiments, the lipid layer consists essentially of the unsaturated phospholipid, cationic lipid, cholesterol, and pegylated phospholipid.

In various embodiments, the API consists essentially of docetaxel and doxorubicin.

In various embodiments, the lipid layer comprises: about 20-75%, preferably about 30-60%, (molar) unsaturated phospholipid; about 10-60%, preferably 20-50%, (molar) cholesterol; about 5-75%, preferably about 10-60%, (molar) cationic lipid; and about 0-20%, preferably 1-10%, (molar) pegylated phospholipid.

In various embodiments, the molar ratio of the lipid layer components:doxorubicin is about 100:1 to about 2:1, preferably about 20:1 to about 5:1; and the molar ratio of the lipid layer components:docetaxel is about 100:1 to about 2:1, preferably about 20:1 to about 5:1.

In various embodiments, the molar ratio of doxorubicin: docetaxel is about 10:1 to 1:10, preferably about 5:1 to 1:5, and more preferably about 2:1 to 1:2.

In various embodiments, the unsaturated phospholipid comprises a polyunsaturated phospholipid or a monounsaturated phospholipid, preferably a phosphatidylcholine, and more preferably and soy phosphatidylcholine or 1,2-dioleoyl-sn-glycero-3-phosphatidylcholine (DOPC).

In various embodiments, the cholesterol comprises a cholesterol derivative, preferably a cationic cholesterol derivative, more preferably an amino cholesterol derivative, and still more preferably dimethylaminoethanecarbamoyl-cholesterol (DC-cholesterol).

In various embodiments, the pegylated phospholipid comprises a phosphoethanolamine, preferably a 1,2-distearoyl-sn-glycero-3-phosphoethanolamine (DSPE) and wherein the pegylation is a PEG 500 to PEG 3000, preferably PEG 2000.

In various embodiments, the plurality of liposomes are comprised in an intravenous formulation.

In various embodiments, the Z-average particle size of the liposomes is about 10-200 nm, preferably about 15-150 nm, and more preferably about 20-120 nm.

In various embodiments, upon intravenous administration to a subject, at least about 10% of the composition is delivered to the liver.

In various embodiments, the pharmaceutical composition is for use as a medicament.

In various embodiments, the pharmaceutical composition is for use as a cancer therapeutic.

In various embodiments, the subject has a cancer. In various embodiments, the cancer is a lung cancer, preferably non-small cell lung cancer (NSCLC); colon cancer; breast cancer; or liver cancer, preferably hepatocellular carcinoma (HCC).

These and other advantages of the present technology will be apparent when reference is made to the accompanying drawings and the following description.

Figure 1:
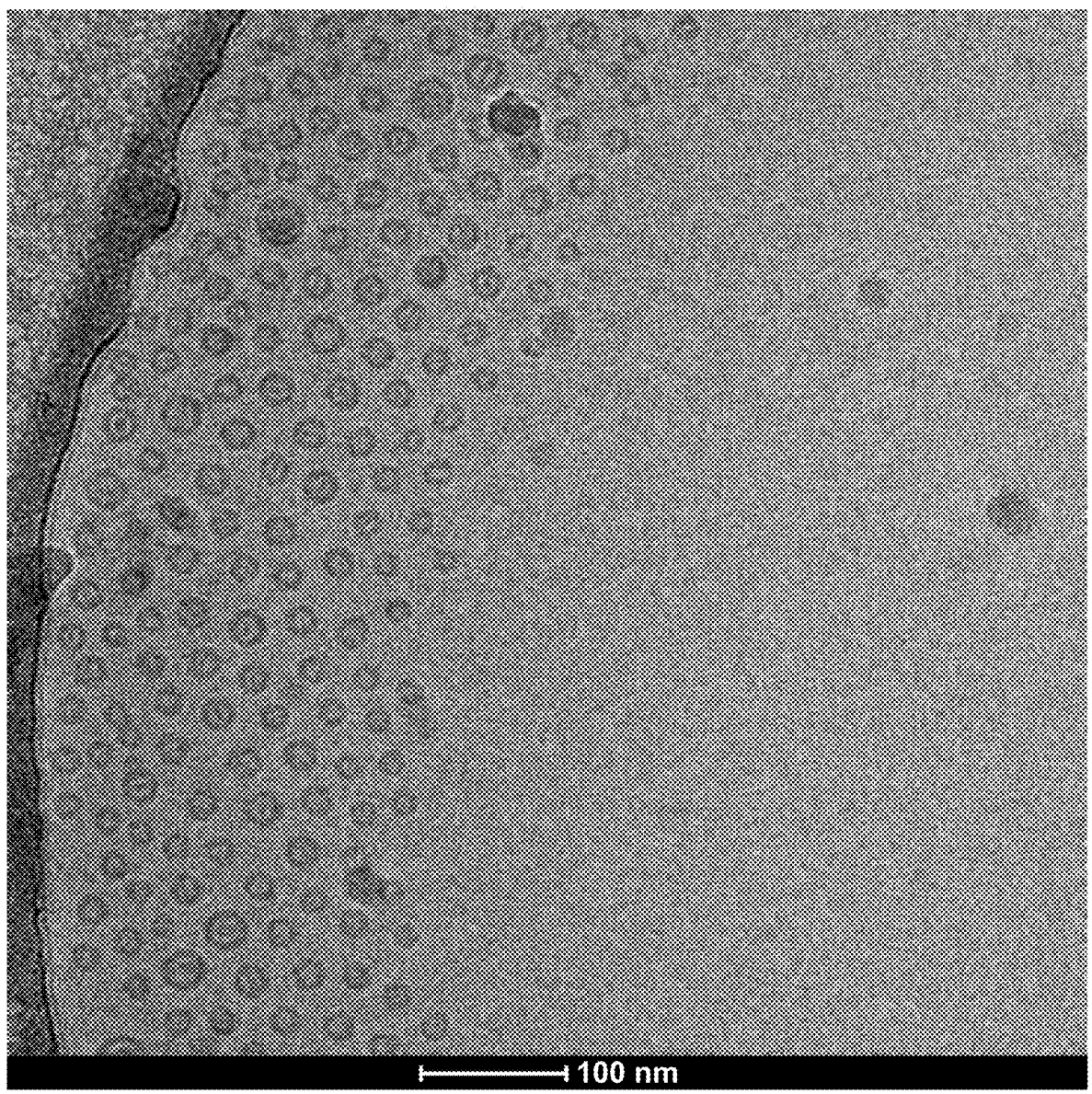
FIG. 1 presents a cryo transmission electron microscopy (TEM) image of liposomal formulation CPT319C.

While the invention comprises embodiments in many different forms, there are shown in the drawings and will herein be described in detail several specific embodiments with the understanding that the present disclosure is to be considered as an exemplification of the principles of the technology and is not intended to limit the invention to the embodiments illustrated.

DETAILED DESCRIPTION

In various aspects and embodiments, the invention provides a pharmaceutical composition including a plurality of liposomes comprising a first drug (e.g., docetaxel) and a second drug (e.g., doxorubicin). In various embodiments, a liposome can include (i) an active pharmaceutical ingredient (API) comprising a first drug (e.g., docetaxel) and a second drug (e.g., doxorubicin); (ii) a lipid layer comprising an unsaturated phospholipid, a cholesterol, and preferably a pegylated phospholipid; and (iii) an aqueous interior, wherein the first drug (e.g., docetaxel) is in the lipid layer and the second drug (e.g., doxorubicin) is crystallized in the aqueous interior. The liposomes can be used to treat a subject, for example, a human subject having cancer.

As described and shown in the examples below, the invention can provide for increased efficacy and/or decreased toxicity, for example relative to (i) other pharmaceutical compositions where one or both of the first drug (e.g., docetaxel) and the second drug (e.g., doxorubicin) are not in a liposomal formulation and/or (ii) other liposomal formulations. The invention can provide for targeted delivery, for example to the liver or avoiding the liver. The invention can mitigate undesired side effects, for example by providing for increased drug loading, thereby reducing the amount of liposomes needed to deliver a quantity of the first drug (e.g., docetaxel) and the second drug (e.g., doxorubicin).

The various features of such liposomes, as well as pharmaceutical compositions including the liposomes and methods of using and making the liposomes are discussed, in turn, below.

Active Pharmaceutical Ingredient (API)

In various aspects and embodiments, the API comprises a first drug (e.g., docetaxel) and a second drug (e.g., doxorubicin). While docetaxel and doxorubicin are presented as illustrative examples, other embodiments are possible where the first drug is in the lipid layer of the liposome and the second drug is in (e.g., crystallized in) the aqueous interior of the liposome. In various embodiments, the API can comprise two (or more) anticancer agents, an anti-inflammatory agents, an anti-diabetic agents, an anti-fungal agents, and/or antibiotic agents.

Docetaxel (as generic or under the trade name Taxotere® or Docecad®) is a clinically well-established anti-mitotic chemotherapy medication that works by interfering with cell division. Docetaxel is approved by the FDA for treatment of locally advanced or metastatic breast cancer, head and neck cancer, gastric cancer, hormone-refractory prostate cancer and non small-cell lung cancer. Docetaxel can be used as a single agent or in combination with other chemotherapeutic drugs as indicated depending on specific cancer type and stage.

Docetaxel is a member of the taxane drug class, which also includes the chemotherapeutic medication paclitaxel. Accordingly, in some embodiments, docetaxel can be substituted for another taxane that can be disposed within the lipid layer of the liposome.

The optimal dose scheduling of taxanes remains unconfirmed, but most studies find significant mortality benefit following either a three-week or a one-week administration schedule. While some research suggests weekly administration as an optimal schedule, the official docetaxel package insert recommends administration every three weeks. Important toxicities to note include neutropenia, febrile neutropenia and neurosensory disturbances. Such toxicities have been well documented in Phase II and Phase III clinical trials and can be anticipated and subsequently managed.

In various embodiments, the invention can increase the efficacy of, and/or decrease undesired side effects from, the docetaxel.

Doxorubicin (trade name Adriamycin®; pegylated liposomal form trade name Doxil®; nonpegylated liposomal form trade name Myocet®), also known as hydroxydaunorubicin and hydroxydaunomycin, is a drug used in cancer chemotherapy and derived by chemical semisynthesis from a bacterial species. It is an anthracycline antibiotic (note: in this context, this does not mean it is used to treat bacterial infections) closely related to the natural product daunomycin and like all anthracyclines, it is believed to work by intercalating DNA, with the most serious adverse effect being life-threatening heart damage. It is commonly used in the treatment of a wide range of cancers, including hematological malignancies (blood cancers, like leukaemia and lymphoma), many types of carcinoma (solid tumors) and soft tissue sarcomas. It is often used in combination chemotherapy as a component of various chemotherapy regimens. In some embodiments, doxorubicin can be substituted for another anticancer agent that can be disposed within the aqueous interior of the liposome.

Common adverse effects of doxorubicin include hair loss (seen in most of those treated with the drug), myelosuppression (a compromised ability of the body's bone marrow to produce new blood cells), nausea and vomiting (which are seen in roughly 30-90% of people treated with the drug), oral mucositis, oesophagitis, diarrhea, skin reactions (including hand-foot syndrome) and localized swelling and redness along the vein in which the drug is delivered. Less common, yet serious reactions include hypersensitivity reactions (including anaphylaxis), radiation recall, heart damage and liver dysfunction.

The drug is administered intravenously, as the hydrochloride salt. It is sold under a number of different brand names, including Adriamycin® PFS, Adriamycin® RDF, or Rubex®. Doxorubicin is photosensitive, and containers are often covered by an aluminum bag and/or brown wax paper to prevent light from affecting it. Doxorubicin is also available in liposome-encapsulated forms as Doxil® (pegylated form), Myocet® (nonpegylated form), and Caelyx®, although these forms must also be given by intravenous injection.

In various embodiments, the invention can increase the efficacy of and/or decrease undesired side effects from, the doxorubicin.

In some embodiments, the API may be a polynucleotide (including an oligonucleotide) a protein or a small molecule.

In one embodiment the API is a polynucleotide. The polynucleotide may be a genomic DNA fragment, cDNA, mRNA, ssRNA, dsRNA, microRNA, siRNA, shRNA, sdRNA, DsiRNA, LNA, and antisense DNA or RNA.

Alternatively, the API may be a small molecule drug. Preferably, the molecule has a molecular weight from about 1500 g/mole to about 50 g/mole.

An API can include, for example, two or more of the following: an anticancer agent, an antibiotic agent, an antiviral agent, an anti-fungal agent, or an analgesic.

Exemplary anticancer agents may include but are not limited acivicin, aclarubicin, acodazole, ametantrone, aminoglutethimide, anthramycin, asparaginase, azacitidine, azetepa, bisantrene, bleomycin, busulfan, cactinomycin, calusterone, caracemide, carboplatin, carfilzomib, carmustine, carubicin, chlorambucil, cisplatin, cyclophosphamide, cytarabine, dacarbazine, dactinomycin, daunorubicin, dezaguanine, diaziquone, docetaxel, doxorubicin, epipropidine, erlotinib, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, paclitaxel, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin.

Exemplary antibiotic agents may include but are not limited to aminoglycoside; amikacin; gentamicin; kanamycin; neomycin; netilmicin; steptomycin; tobramycin; ansamycins; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromycin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil (archaic); sulfacetamide; sulfamethizole; sufanilimide (archaic); sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin;

polymyxin, purazinamide; quinupristin/dalfopristin; rifampin or rifampicin; and timidazole.

In specific embodiments, the anti-cancer agent is chosen from daunorubicin, doxorubicin, paclitaxel, docetaxel, cisplatin, carboplatin, cytarabine, floxuridine, fludarabine, fluorouracil, iproplatin, leuprolide acetate, carfilzomib, and methotrexate.

Exemplary antiviral agents may include, but are not limited to thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscamet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitor; zanamivir; oseltamivir; moroxydine; inosine pranobex; pleconaril; and enfuvirtide.

Exemplary anti-fungal agents may include but are not limited to allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Colloidal Dispersion (ABCD); and griseofulvin.

Exemplary analgesics may include, but are not limited to opiate derivative, codeine, meperidine, methadone, and morphine.

In various embodiments, the API consists essentially of the first drug (e.g., docetaxel) and the second drug (e.g., doxorubicin).

In various embodiments, the molar ratio of the lipid layer components:second drug (e.g., doxorubicin) is about 100:1 to about 5:1, preferably about 20:1 to about 10:1; and the molar ratio of the lipid layer components:first drug (e.g., docetaxel) is about 100:1 to about 5:1, preferably about 20:1 to about 10:1.

In various embodiments, the molar ratio of second drug (e.g., doxorubicin):first drug (e.g., docetaxel) is about 10:1 to 1:10, preferably about 5:1 to 1:5, and more preferably about 3:1 to 1:3.

The Lipid Layer and Aqueous Solutions

The invention utilizes lipid and aqueous solutions, for example in making liposomes in accordance with the invention. Accordingly, the composition lipid and/or aqueous solutions can affect the final composition of the liposomes.

In various embodiments, the lipid solution may comprise an organic solvent. The organic solvent may be a water miscible solvent. Preferably, the water miscible solvent is selected from the group consisting of ethanol, methanol, DMSO and isopropanol. Most preferably, the organic solvent is ethanol.

As used herein the term of "cationic lipid" refers to a lipid or a cholesterol derivative that carries a net positive charge at about pH 3-pH 9.

As used herein the term of "anionic lipid" refers to a lipid or a cholesterol derivative that carries a net negative charge at about pH 3-pH 9.

As used herein the term "pegylated lipid" refers to a lipid that is conjugated with a polyethylene glycol polymer.

As used herein the term "neutral lipid" refers to the lipid that does not carry net charge at about pH 3-pH 9.

The lipid solution may include a mixture of lipids. The mixture of lipids preferably includes cholesterol.

The mixture of lipids may also include a cationic lipid. The cationic lipid may be, but is not limited to, N,N-dioleyl-N,N-dimethylammonium chloride ("DODAC"); N-(2,3-dioleyloxy)propyl)-N,N,N-trimethylammonium chloride ("DOTMA"); N-(2,3-dioleyloxy)propyl)-N,N-dimethylammonium chloride ("DODMA"); N,N-distearyl-N,N-dimethylammonium bromide ("DDAB"); N-(2,3-dioleoyloxy)propyl)-N,N,N-trimethylammonium chloride ("DOTAP"); N-(2,3-dioleoyloxy)propyl)-N,N-dimethylammonium chloride ("DODAP"); 3-(N-(N',N'-dimethylaminoethane)carbamoyl)cholesterol ("DC-Chol"); N-(1,2-dimyristyloxyprop-3-yl)-N,N-dimethyl-N-hydroxyethyl ammonium bromide ("DMRIE"); 1.2-dilinoleyloxy-N,N-dimethyl-3-aminopropane (DLinDMA); 1,2-distearyloxy-N,N-dimethyl-3-aminopropane (DSDMA); 1.2-dilinolenyloxy-N,N-dimethyl-3-aminopropane (DLenDMA); 2-{4-[(3b)-cholest-5-en-3-yloxy]butoxy}-N,N-dimethyl-3-[(9Z,12Z)-octadeca-9,12-dien-1-yloxy]propan-amine (CLinDMA).

In some embodiments the mixture of lipids may include an anionic lipid. The anionic lipid may be but is not limited to diacylglycerol phophatidic acid (1,2-distearoyl-sn-glycero-3-phosphate (DSPA); 1,2-dipalmitoyl-sn-glycero-3-phosphate (DPPA); 1,2-dimyristoyl-sn-glycero-3-phosphate (DMPA); 1,2-dilauroyl-sn-glycero-3-phosphate (DLPA); 1,2-dioleoyl-sn-glycero-3-phosphate (DOPA)), diacylglycerol phosphoglycerol (1,2-distearoyl-sn-glycero-3-phospho-(1'-rac-glycerol) (DSPG); 1,2-dipalmitoyl-sn-glycero-3-phospho-(1'-rac-glycerol) (DPPG); 1,2-dimyristoyl-sn-glycero-3-phospho-(1'-rac-glycerol) (DMPG); 1,2-dilauroyl-sn-glycero-3-phospho-(1'-rac-glycerol) (DLPG); 1,2-dioleoyl-sn-glycero-3-phospho-(1'-rac-glycerol) (DOPG)), phosphatidylglycerol, cardiolipin, diacylphosphatidylserine, N-succinyl phosphatidylethanolamines, N-glutarylphosphatidylethanolamines, lysylphosphatidylglycerols, and other anionic modifying groups joined to neutral lipids. The mixture of lipids may also include a neutral lipid. The neutral lipid may be but is not limited to diacylglycerol phosphocholine (L-α-phosphatidylcholine, hydrogenated (Soy) (HSPC); diacylglycerol phosphocholine (L-α-phosphatidylcholine, (Soy) (Soy PC), 1,2-distearoyl-sn-glycero-3-phosphocholine (DSPC); 1,2-dipalmitoyl-sn-glycero-3-phosphocholine (DPPC); 1,2-dimyristoyl-sn-glycero-3-phosphocholine (DMPC); 1,2-dilauroyl-sn-glycero-3-phosphocholine (DLPC); 1,2-dioleoyl-sn-glycero-3-phosphocholine (DOPC), diacylglycerol phosphoethanolamine (1,2-distearoyl-sn-glycero-3-phosphoethanolamine (DSPE); 1,2-dipalmitoyl-sn-glycero-3-phosphoethanolamine (DPPE); 1,2-dimyristoyl-sn-glycero-3-phosphoethanolamine (DMPE); 1,2-dilauroyl-sn-glycero-3-phosphoethanolamine (DLPE); 1,2-dioleoyl-sn-glycero-3-phosphoethanolamine (DOPE), and phosphatidylserine.

The mixture of lipids may also include a pegylated lipid. The pegylated lipid may be but is not limited to 1,2-distearoyl-sn-glycero-3-phosphoethanolamine-N-[methoxy(polyethylene glycol)-2000] (mPEG-2000-DSPE); 1,2-dioctadecanoyl-sn-glycero-3-phosphoethanolamine-N-[methoxy(polyethylene glycol)-2000] (mPEG-2000-DOPE); 1,2-dipalmitoyl-sn-glycero-3-phosphoethanolamine-N-[methoxy(polyethylene glycol)-2000] (mPEG-2000-DPPE); 1,2-dimyristoyl-sn-glycero-3-phosphoethanolamine-N-[methoxy(polyethylene glycol)-2000] (mPEG-2000-DMPE); 1,2-dilauroyl-sn-glycero-3-phosphoethanolamine-N-[methoxy(polyethylene glycol)-2000] (mPEG-2000-DLPE); 1,2-distearoyl-sn-glycero-3-phosphoethanolamine-N-[methoxy(polyethylene glycol)-

5000] (mPEG-5000-DSPE); 1,2-dioctadecanoyl-sn-glycero-3-phosphoethanolamine-N-[methoxy(polyethylene glycol)-5000] (mPEG-5000-DOPE); 1,2-dipalmitoyl-sn-glycero-3-phosphoethanolamine-N-[methoxy(polyethylene glycol)-5000] (mPEG-5000-DPPE); 1,2-dimyristoyl-sn-glycero-3-phosphoethanolamine-N-[methoxy(polyethylene glycol)-5000] (mPEG-5000-DMPE); 1,2-dilauroyl-sn-glycero-3-phosphoethanolamine-N-[methoxy(polyethylene glycol)-5000] (mPEG-5000-DLPE).

The mixture of lipid may also include a lipid-like molecule or lipidoid. The mixture of lipid may also include a lipid- or cholesterol-conjugated molecule including a protein, or a peptide, or an oligonucleotide.

In various embodiments, the lipid layer includes one or more of the lipid components disclosed herein.

In various embodiments, the lipid layer consists essentially of the unsaturated phospholipid and cholesterol.

In various embodiments, the lipid layer consists essentially of the unsaturated phospholipid, cholesterol, and pegylated phospholipid.

In various embodiments, the lipid layer comprises: about 20-75%, preferably about 30-60%, (molar) unsaturated phospholipid; about 10-60%, preferably 20-50%, (molar) cholesterol; and about 0-20%, preferably 1-10%, (molar) pegylated phospholipid.

In various embodiments, the molar ratio of the lipid layer components:doxorubicin is about 100:1 to about 5:1, preferably about 20:1 to about 10:1; and the molar ratio of the lipid layer components:docetaxel is about 100:1 to about 5:1, preferably about 20:1 to about 10:1.

In various embodiments, the molar ratio of doxorubicin:docetaxel is about 10:1 to 1:10, preferably about 5:1 to 1:5, and more preferably about 3:1 to 1:3.

In various embodiments, the unsaturated phospholipid comprises a polyunsaturated phospholipid or a monounsaturated phospholipid, preferably a phosphatidylcholine, and more preferably and soy phosphatidylcholine or 1,2-dioleoyl-sn-glycero-3-phosphatidylcholine (DOPC).

In various embodiments, the cholesterol comprises a cholesterol derivative, preferably a cationic cholesterol derivative, more preferably an amino cholesterol derivative, and still more preferably dimethylaminoethanecarbamoyl-cholesterol (DC-cholesterol).

In various embodiments, the pegylated phospholipid comprises a phosphoethanolamine, preferably a 1,2-distearoyl-sn-glycero-3-phosphoethanolamine (DSPE) and wherein the pegylation is a PEG 500 to PEG 5000, preferably PEG 2000.

In various embodiments, the composition of the lipid layer is tuned to achieve a desired loading of the first drug. Although at least a fraction of the first drug is in the lipid layer, one of ordinary skill will understand that the first drug will have a partition coefficient between the lipid layer and aqueous interior. In some embodiments, essentially all of the first drug will be in the lipid layer.

The aqueous solution of the process preferably includes water and a buffer. Buffers may be of but are not limited to phosphate, histidine, HEPES, Tris, acetate, carbonate, and citrate. In various embodiments, the composition of the aqueous solution is tuned to achieve a desired loading (and/or crystallization) of the second drug. Although at least a fraction of the second drug is in the aqueous interior of the liposome, one of ordinary skill will understand that the second drug will have a partition coefficient between the lipid layer and aqueous interior. In some embodiments, essentially all of the second drug will be in the aqueous interior.

Methods for Making Liposomes

Examples of apparatuses and methods that can be adapted for making the liposomes of the invention can be found, for example, in U.S. patent application Ser. No. 14/209,187 (and published as US20140348900), which is herein incorporated by reference in its entirety. A description of a number of different methods of making liposomes in accordance with the invention are presented in the Examples below.

The invention provides a method of making the liposome according to any of the aspects or embodiments disclosed herein, or the pharmaceutical composition according to any of the aspects or embodiments disclosed herein, comprising: (i) introducing a lipid solution of an unsaturated phospholipid, cholesterol, a first drug (e.g., docetaxel), and preferably a pegylated phospholipid in ethanol through a first port into a mixing chamber and an aqueous solution through a second port into the mixing chamber, thereby making a plurality of liposomes; and (ii) incubating the plurality of liposomes in a second drug (e.g., doxorubicin) solution.

In various embodiments, the angle between at least one lipid and at one aqueous solution inlet ports is not 180° or a substantially similar angle. In some aspects, at least one stream of lipid solution and at one stream of aqueous solution collide at an angle less than about 180°. Thus, in some aspects, the method does not include a T-connector.

In some embodiments, the angle between at least one lipid and at one aqueous solution inlet ports is about 120° or less, e.g., 115° or less, 100° or less, 90° or less, 80° or less, 72° or less, 60° or less, 45° or less, 30° or less, 18° or less, In some embodiments, the aqueous solution in step ii) is introduced via at least two inlet ports, e.g., at least 3, 4, 5, 6, 7, 8, 9, 10, 11, 12, 13, 14, 15, 16, 17, 18, 19, 20 or more. In some embodiments, the aqueous solution in step ii) is introduced via at least 3 but no more than 11 inlet ports, e.g., at least 3 but not more than 7, at least 3 but no more than 5, at least 4 but no more than 11, at least 5 but no more than 11, at least 6 but no more than 11.

In some embodiments, at least two (e.g., 3, 4, 5, 6, 7, etc.) aqueous inlet ports and at least one (e.g., 2, 3, 4, 5, etc.) lipid solution inlet port are in the same plane.

In some embodiments, at least one (e.g., 2) outlet port is substantially perpendicular to the plane of inlet ports. In other embodiments, at least one (e.g., 2, 3, 4, 5, etc.) outlet port is substantially not perpendicular to the plane of inlet ports.

In some embodiments, at least two (e.g., 3, 4, 5, 6, 7, etc.) aqueous solution inlet ports and at least one (e.g., 2, 3, 4, 5, etc.) lipid solution inlet port are not in the same plane.

Preparing Lipid Solutions

The lipid solution may be made from the stock solutions of individual lipids that are mixed together. Lipids are preferably dissolved in an organic solvent to make a lipid solution. The organic solvent used for making the lipid solution may be miscible with water. Preferably the solvent may ethanol, methanol, DMSO, propanol, DMF, THF, acetone, dioxane, ethylene glycol, polyethylene glycol and isopropanol. More preferably, the solvent is polyethylene glycol, isopropanol, and ethanol. Preferably, the solvent includes less than 10% water. In some cases, the lipid solution may be made from a mixture of lipids, thereupon dissolving the mixture in an organic solvent. The concentration of the total lipids in the solution may be in the range from about 1 mg/mL to about 200 mg/mL, e.g., from about 1 mg/mL to about 100 mg/mL. More preferably, the concentration of the total lipids in the solution may be in the range from about 5 mg/mL to about 100 mg/mL or form about 10 mg/mL to 100 mg/mL. In some embodiments, the organic solvent is ethanol at a concentration of about 70% or more (e.g., 75% or more, 80% or more, 85% or more, 90% or more, 95% or more, 100%).

The mixture of lipids will be optimized as required for optimal delivery of the API and is readily optimized by routine experimentation by one of ordinary skill in the art.

In certain embodiments, a water-insoluble API may be dissolved in the lipid solution. The concentration of the API in the lipid solution will depend on the efficacy of the agent and may easily be determined by one of ordinary skill in the art. The lipid/API ratio will determined by the encapsulation power of the liposome to the API.

Preparing Aqueous Solutions

A water-soluble API component may be dissolved in a first aqueous solution (S1). The pH and salinity of the solution may be optimized to accommodate the requirements for the interaction between the API component and the lipids to form liposome. These conditions may be readily determined by one of ordinary skill in the art. Samples are provided in the Examples below. As will be readily apparent to those of skill in the art, an aqueous solution that lacks an API, referred to as (S2), may be similar to a solution having the agent. Alternatively, S1 and S2 may be different.

Liposome Preparation, Mixing the Solutions

The lipid solution and the aqueous solution(s) preferably enter the manifold from different ports, each with a flow rate of from about 1 mL/min to about 6000 mL/min. Preferably, the flow rates may be from about 5 mL/min to about 1000 mL/min. More preferably, the rates may be from about 20 mL/min to about 600 mL/min. In some embodiments, the flow rates are adjusted based on the size of inlet ports to obtain the desired liposome size, morphology, PDI, and manufacturing scales.

In some embodiments, the lipid solution and/or the aqueous solution is introduced via port size of 0.1-5.0 mm at a flow rate about 1 mL/min to about 2,500 mL/min.

In some embodiments, the flow velocity of the lipid solution and/or the aqueous solution is from about 0.02 m/s to about 40 m/s, e.g., from 0.1 m/s to 30 m/s, from 0.2 m/s to 20 m/s. The flow velocity is adjusted based on the size of inlet ports to obtain the desired liposome size, morphology, PDI, and manufacturing scale.

Loading of the API Into Liposome

In the mixing chamber the lipids are believed to instantaneously assemble into liposome particles. When the drug API is carried by the lipid solution or by aqueous solution, it may be encapsulated in the liposome by either lipophilic or electrostatic interaction, or both, between the API and the lipids.

The present invention also provides a method of producing liposome that do not contain an API (so-called "empty" liposome). In such embodiments, the API is absent from both the lipid solution and the aqueous solution that are mixed in the manifold. The API may be loaded into the liposomes by the process of diffusion or another process. For example, doxorubicin may be loaded into the liposome with a pH gradient. See U.S. patent application Ser. No. 10/019,200, PCT Publication No. WO 2001/005373, U.S. Pat. Nos. 5,785,987, 5,380,531, 5,316,771, and 5,192,549, all of which are incorporated herein by reference.

Preferably, the API is mixed with a liposome solution to upload the API into the liposome by diffusion. In one aspect, the API is dissolved in an aqueous solution, and the solution is mixed with the empty liposome. In another aspect, the API may be readily soluble in the solution of empty liposome, and therefore, the API may be directly mixed with the solution of the empty liposome.

The volume ratio of the solution of the API to the empty liposome solution of the API is preferably in the range from about 1:50 to about 1:1. A lower volume of the solution is preferred because it avoids a significant dilution to the final liposome solution.

The drug encapsulation efficiency is preferably greater than 70%. More preferably the efficiency is greater than 80%. Most preferably, the efficiency is greater than 90%.

Liposome Concentration Adjustment

Tangent flow filtration may be used to concentrate the liposome solution.

Buffer Change

Residual organic solvent in the liposome solution may be removed by a buffer change. Preferably, the buffer change is performed by tangent flow filtration. In another embodiment, the buffer change may be performed by dialysis.

Sterile Filtration

The liposome solutions can be sterilized, for example, by passing the solution through a 0.22 micron sterile filter.

Liposomes

In various embodiments, the Z-average particle size of the liposomes is about 10-200 nm, preferably about 15-150 nm, and more preferably about 20-120 nm.

Preferably, more than 70% of API is encapsulated in the liposomes. More preferably, more than 80% of API is encapsulated in the liposomes, most preferably, more than 90% of API is encapsulated in the liposomes.

Optionally, liposomes can be unilamellar. Alternatively, the liposomes can be of multilamellar, or of inverted hexagonal or cubic morphology, or as lipid discs, or hollow liposomes.

In some embodiments, the mean particle size of the liposomes is from about 10 nm to about 2,000 nm, preferably less than 300 nm, more preferably, the mean particle size may be about 10 to 300 nm or about 20 to about 300 nm. Most preferably, the mean particle size is about 20 to 120 nm In some embodiments, the liposomes have a polydispersity index from about 0.005 to about 0.8, e.g., 0.005 to about 0.5, 0.01 to about 0.5, 0.01 to about 0.4, 0.01 to about 0.2.

Pharmaceutical Compositions

In various embodiments, the pharmaceutical composition is for use as a medicament. In various embodiments, the pharmaceutical composition is for use as a cancer therapeutic. In various embodiments, the pharmaceutical composition can include one or more antibiotic, antivirus, anti-diabetes, anti-hypertension, anti-fungal, or analgesic.

In various embodiments, the plurality of liposomes are comprised in an injectable formulation, for example, by subcutaneous, intravenous, intramuscular, intrathecal or intraperitoneal injection. Injectable formulations can be aqueous solutions, preferably in physiologically compatible buffers such as Hanks' solution, Ringer's solution, or physiological saline buffer. The injectable formulation can contain formulatory agents such as suspending, stabilizing and/or dispersing agents. Alternatively, the liposomes can be in a dried or powder form for constitution with a suitable vehicle, e.g., sterile pyrogen-free water, before use.

Treatment and Administration

The invention provides a method comprising administering the liposome according to any of the aspects or embodiments disclosed herein, or the pharmaceutical composition according to any of the aspects or embodiments disclosed herein, to a subject.

The invention also provides a method of treating a subject comprising administering an effective amount of the liposome according to any of the aspects or embodiments disclosed herein, or the pharmaceutical composition according to any of the aspects or embodiments disclosed herein, to a subject.

Accordingly, the invention provides methods for treating cancer cells and/or tissue, including cancer cells and/or tissue in a human subject. Cancer can be caused by malignant tumors formed by an abnormal growth of cells and tissue leading to organ failure.

Solid tumors can be neoplasms (new growth of cells) or lesions (damage of anatomic structures or disturbance of physiological functions) formed by an abnormal growth of body tissue cells other than blood, bone marrow or lymphatic cells. A solid tumor consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

The subject being treated may have been diagnosed with cancer. The subject may have locally advanced, unresectable, or metastatic cancer and/or may have failed a prior first-line therapy. In various embodiments, the cancer is liver cancer (e.g., hepatocellular carcinoma, HCC). In various embodiments, the liver cancer (e.g., HCC) can be intermediate, advanced, or terminal stage. The liver cancer (e.g., HCC) can be metastatic or non-metastatic. Liver cancer can include a liver tumor resulting from the metastasis of a non-liver cancer, to the liver. The liver cancer (e.g., HCC) can be resectable or unresectable. The liver cancer (e.g., HCC) can comprise a single tumor, multiple tumors, or a poorly defined tumor with an infiltrative growth pattern (into portal veins or hepatic veins). The liver cancer (e.g., HCC) can comprise a fibrolamellar, pseudoglandular (adenoid), pleomorphic (giant cell), or clear cell pattern. The liver cancer (e.g., HCC) can comprise a well differentiated form, and tumor cells resemble hepatocytes, form trabeculae, cords, and nests, and/or contain bile pigment in cytoplasm. The liver cancer (e.g., HCC) can comprise a poorly differentiated form, and malignant epithelial cells are discohesive, pleomorphic, anaplastic, and/or giant. In some embodiments, the liver cancer (e.g., HCC) is associated with hepatitis B, hepatitis C, cirrhosis, or type 2 diabetes.

In various embodiments, the cancer is a lung cancer, preferably non-small cell lung cancer (NSCLC); colon cancer; breast cancer; or liver cancer, preferably hepatocellular carcinoma (HCC).

In various embodiments, the docetaxel can be in a concentration of 10, 20, 30, 40, 50, 75, 80, 100, 125, 150, or 160 mg/mL. A dose can be about 10 mg/m$^2$ to 150 mg/m$^2$ (e.g., 10, 20, 25, 30, 40, 50, 60, 70, 75, 80, 90, 100, 110, 120, 125, 130, 140, or 150 mg/m$^2$). For example, a dose can be 75 mg/m$^2$. A dose can be administered every 3 weeks for 1, 2, 3, 5, 5, or 6 cycles. One skilled in the art will appreciate that dosing guidelines for docetaxel are known in the art, and can be adapted based upon factors including, but not limited to the cancer type, the cancer stage, the dosing regimen, the dose of doxorubicin, and/or the efficacy of the pharmaceutical formulations of the invention.

In various embodiments, the doxorubicin can be in a concentration of 0.1, 0.5, 1, 1.5, 2, 3, 4, or 5 mg/mL. A dose can be about 1 mg/m$^2$ to 100 mg/m$^2$ (e.g., 1, 2, 3, 4, 5, 6, 7, 8, 9, 10, 20, 25, 30, 40, 50, 60, 70, 75, 80, 90, or 100 mg/m$^2$). For example, a dose can be 30 mg/m$^2$. A dose can be administered every 3 weeks for 1, 2, 3, 5, 5, or 6 cycles. One skilled in the art will appreciate that dosing guidelines for docetaxel are known in the art, and can be adapted based upon factors including, but not limited to the cancer type, the cancer stage, the dosing regimen, the dose of doxorubicin, and/or the efficacy of the pharmaceutical formulations of the invention.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

Example 1: Preparation of Liposomal Formulation CPT307C

CPT307 comprises of a nonsaturated lipid 1,2-Dioleoyl-sn-glycero-3-Phosphatidylcholine (DOPC), cholesterol, and 1,2-distearoyl-sn-glycero-3-phosphoethanolamine-N-[methoxy9polyethyleneglycol)-2000] (mPEG2000-DSPE). It was found that compared the saturated lipid, the nonsaturated lipid has a greater capacity to encapsulate docetaxel. Liposomal formulation CPT307B was prepared by first dissolving 2100 mg of DOPC, 280 mg of cholesterol, 700 mg of mPEG2000-DSPE, and 175 mg of docetaxel (DOCE) in 70 mL of anhydrous ethanol. The composition (% molar) of the CPT307B lipid solution is illustrated in Table 1. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass vial. The liposome was concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter. The Z-average particle size was 32.9 nm.

CPT307C was prepared by loading doxorubicin (DXR) into CPT307B. Fourteen milliliters of CPT307B containing 36 mg/mL of DOCE was mixed with 24 mg of DXR that had been pre-dissolved in the histidine/sucrose buffer, and incubated at 42° C. for 3 hours. The DOCE and DXR dual-loaded liposome was then sterilized by filtration through a 0.22 μm filter. The composition (% molar) of the CPT307C lipid solution is illustrated in the Table 1, 99.6% of DXR was encapsulated. The molar ratio of DOCE:DXR was 1:1.

TABLE 1

Lipid Compositions of Example 1.

| Component | CPT307B % (molar)* | CPT307C % (molar)* |
|---|---|---|
| DOPC | 73.6 | 73.6 |
| Cholesterol | 20 | 20 |
| mPEG2000-DSPE | 6.4 | 6.4 |
| DOCE | 6.0 | 6.0 |
| DXR | 0 | 6.0 |

*The value represents the molar % of each component vs. total lipids.

Example 2: Preparation of Liposomal Formulation CPT308C

Different from CPT307C in Example 1, CPT308C contains a polyunsaturated lipid L-α-phosphatidylcholine (Soy PC) that has a high capacity to encapsulate DOCE. Two milliliters of lipids/DOCE solution was prepared by dissolving 30 mg of Soy PC, 10 mg of cholesterol, 10 mg of mPEG2000-DSPE, and 6 mg of DOCE in anhydrous ethanol. The composition (% molar) of the liposomal formulation CPT308C lipid solution is illustrated in Table 2. In addition, three aqueous solutions of 250 mM ammonium sulfate, pH 6.5 were used. Two milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass vial. The buffer was changed into a histidine/sucrose buffer (10 mM histidine, 9.2% sucrose, pH 6.5) by dialysis. The formulation was then sterilized by filtration through a 0.22 µm filter.

The DOCE loaded liposome was then mixed with DXR that had been pre-dissolved in the histidine/sucrose buffer at a doxorubicin/lipid ratio (w/w) of 1:10, and incubated at 42° C. for 2 hours, 97% of DXR was encapsulated. The DOCE and DXR dual-loaded liposome was then sterilized by filtration through a 0.22 µm filter. The Z-average particle size of the dual-loaded liposome was 38.2 nm for CPT308C.

TABLE 2

Lipid Composition of Example 2.

| Component | CPT308C % (molar) * |
|---|---|
| Soy PC | 56.8 |
| Cholesterol | 38.0 |
| mPEG2000-DSPE | 5.2 |
| DOCE | 13.5 |
| DXR | 10.9* |

* The value represents the molar % of each component vs. total lipids.

Example 3: Preparation of Liposomal Formulation CPT309C

CPT309C contains the polyunsaturated lipid Soy PC at a higher molar ratio than CPT308C in Example 2 and thus showed a greater capacity to encapsulate DEOCE. Two milliliters of lipids/DOCE solution was prepared by dissolving 30 mg of L-α-phosphatidylcholine (Soy PC), 4 mg of cholesterol, 10 mg of mPEG2000-DSPE, and 6 mg of DOCE in anhydrous ethanol. The composition (% molar) of the liposomal formulation CPT309C lipid solution is illustrated in Table 3. In addition, three aqueous solutions of 250 mM ammonium sulfate, pH 6.5 were used. Two milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass vial. The buffer was changed into a histidine/sucrose buffer (10 mM histidine, 9.2% sucrose, pH 6.5) by dialysis. The formulation was then sterilized by filtration through a 0.22 µm filter.

The DOCE loaded liposome was then mixed with DXR that had been pre-dissolved in the histidine/sucrose buffer at a doxorubicin/lipid ratio (w/w) of 1:10, and incubated at 42° C. for 2 hours, 98.8% of DXR was encapsulated. The DOCE and DXR dual-loaded liposome was then sterilized by filtration through a 0.22 µm filter. The Z-average particle size of the dual-loaded liposome was 38.6 nm for CPT309C.

TABLE 3

Lipid Composition of Example 3.

| Component | CPT309C % (molar)* |
|---|---|
| Soy PC | 73.6 |
| Cholesterol | 19.7 |
| mPEG2000-DSPE | 6.8 |
| DOCE:Lipids | 17.5 |
| DXR:Lipids | 14.1 |

*The value represents the molar % of each component vs. total lipids.

Example 4: Preparation of Liposomal Formulation CPT311C

CPT311C is a cationic liposome as it contains a cationic derivative of cholesterol (DC-cholesterol). It was found that cationic lipids enhances liver-targeting delivery and anti-tumor efficacy of the therapeutic agent in the liposome. Two milliliters of lipids/DOCE solution (liposomal formulation CPT311B) was prepared in anhydrous ethanol to give concentrations of 15 mg/mL DOPC, 9.3 mg/mL of 3β-[N-(N', N'-dimethylaminoethane)-carbamoyl]cholesterol hydrochloride (DC-Cholesterol), 5 mg/mL of mPEG2000-DSPE, and 2.0 mg/mL of DOCE. The composition (% molar) of the CPT311B lipid solution is illustrated in Table 4. In addition, three aqueous solutions of 250 mM ammonium sulfate, pH 6.5 were used. Two milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass vial. The buffer was changed into a histidine/sucrose buffer (10 mM histidine, 9.2% sucrose, pH 6.5) by dialysis. The formulation was then sterilized by filtration through a 0.22 µm filter. The Z-average particle size was 34.5 nm.

Liposomal formulation CPT311C was prepared by loading doxorubicin (DXR) into CPT311B. Two milliliters of CPT311B was mixed with 0.5 mg of DXR that had been pre-dissolved in the histidine/sucrose buffer at 10 mg/mL, and incubated at 42° C. for 2 hours, 94.5% of DXR was encapsulated. The DOCE and DXR dual-loaded liposome was then sterilized by filtration through a 0.22 µm filter. The composition (% molar) of the CPT311C is illustrated in Table 4. The Z-average particle size of the dual-loaded liposome was 34.9 nm for CPT311C.

TABLE 4

Lipid Compositions of Example 4.

| Component | CPT311B % (molar)* | CPT311C % (molar)* |
|---|---|---|
| DOPC | 50 | 50 |
| DC-Cholesterol | 45 | 45 |
| mPEG2000-DSPE | 5 | 5 |
| DOCE | 6.5 | 6.5 |
| DXR | 0 | 4.8 |

*The value represents the molar % of each component vs. total lipids.

It was found that the cationic surface charge of liposome promotes liposome delivery to the liver. The alternation of the molar ratio of the cationic lipid, for example, DC-cholesterol in the liposome, controls the liver delivery of liposome and the clearance rate from the blood. The following examples (from Examples 5 to Example 7) comprise of DOCE, cholesterol, DC-cholesterol, and mPEG2000-DSPE with increased molar ratio of DC-cholesterol (from 3.9% increased to 15.4%) and deceased cholesterol molar ratio (from 34.4% reduced to 17.8%) while the molar ratio of DOPC and mPEG2000-DSPE remain unchanged or a minorly changed.

Example 5: Preparation of Liposomal Formulation CPT315C

Two and one half (2.5) milliliters of lipids/DOCE solution was prepared by dissolving 37.5 mg DOPC, 11.3 mg cholesterol, 1.4 mg of 3β-[N-(N',N'-dimethylaminoethane)-carbamoyl]cholesterol hydrochloride (DC-Cholesterol), 12.5 mg mPEG2000-DSPE, and 4 mg DOCE in 2.5 mL anhydrous ethanol. In addition, three aqueous solutions of 250 mM ammonium sulfate, pH 6.5 were used. Two and one half (2.5) milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass vial. The buffer was changed into a histidine/sucrose buffer (10 mM histidine, 9.2% sucrose, pH 6.5) by dialysis.

The DOCE loaded liposome was then mixed with DXR that had been pre-dissolved in the histidine/sucrose buffer at a doxorubicin/lipid ratio (w/w) of 1:16, and incubated at 42° C. for 2 hours, 96.9% of DXR was encapsulated. The DOCE and DXR dual-loaded liposome was then sterilized by filtration through a 0.22 μm filter. The Z-average particle size of the dual-loaded CPT315C was 35.1 nm.

TABLE 5

Lipid Composition of Example 5.

| Component | CPT315C % (molar)* |
|---|---|
| DOPC | 56.4 |
| Cholesterol | 34.4 |
| DC-Cholesterol | 3.9 |
| mPEG2000-DSPE | 5.3 |
| DOCE | 7.2 |
| DXR | 7.3 |

*The value represents the molar % of each component vs. total lipids.

Example 6: Preparation of Liposomal Formulation CPT317C

Twenty milliliters of lipids/DOCE solution was prepared by dissolving 600 mg of DOPC, 140 mg of cholesterol, 84 mg of DC-Cholesterol, 200 mg of mPEG2000-DSPE, and 50 mg of DOCE in anhydrous ethanol. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass bottle and then was concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter. Liposomal formulation CPT317B loaded with DOCE was obtained. The Z-average particle size of CPT317B was 37.5 nm.

Liposomal formulation CPT317C was prepared by loading doxorubicin (DXR) into CPT317B. Five milliliters of CPT317B was mixed with 5.2 mg of DXR, and incubated at 42° C. for 3 hours. The DOCE and DXR dual-loaded liposome was then sterilized by filtration through a 0.22 μm filter. The composition (% molar) of the CPT317C lipid solution is illustrated in Table 6. 99.8% of DXR was encapsulated.

TABLE 6

Lipid Composition of Example 6.

| Component | CPT317C % (molar)* |
|---|---|
| DOPC | 56.4 |
| Cholesterol | 26.7 |
| DC-Cholesterol | 11.6 |
| mPEG2000-DSPE | 5.3 |
| DOCE | 4.5 |
| DXR | 4.5 |

*The value represents the molar % of each component vs. total lipids.

Example 7: Preparation of Liposomal Formulation CPT319C

The lipids/DOCE solution was prepared by dissolving 1848 mg of DOPC, 303 mg of cholesterol, 423 mg of DC-Cholesterol, 605 mg of mPEG2000-DSPE, and 154 mg of DOCE in 61.5 mL of anhydrous ethanol. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass bottle and then was concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter to obtain liposomal formulation CPT319B loaded with DOCE.

Figure 2:
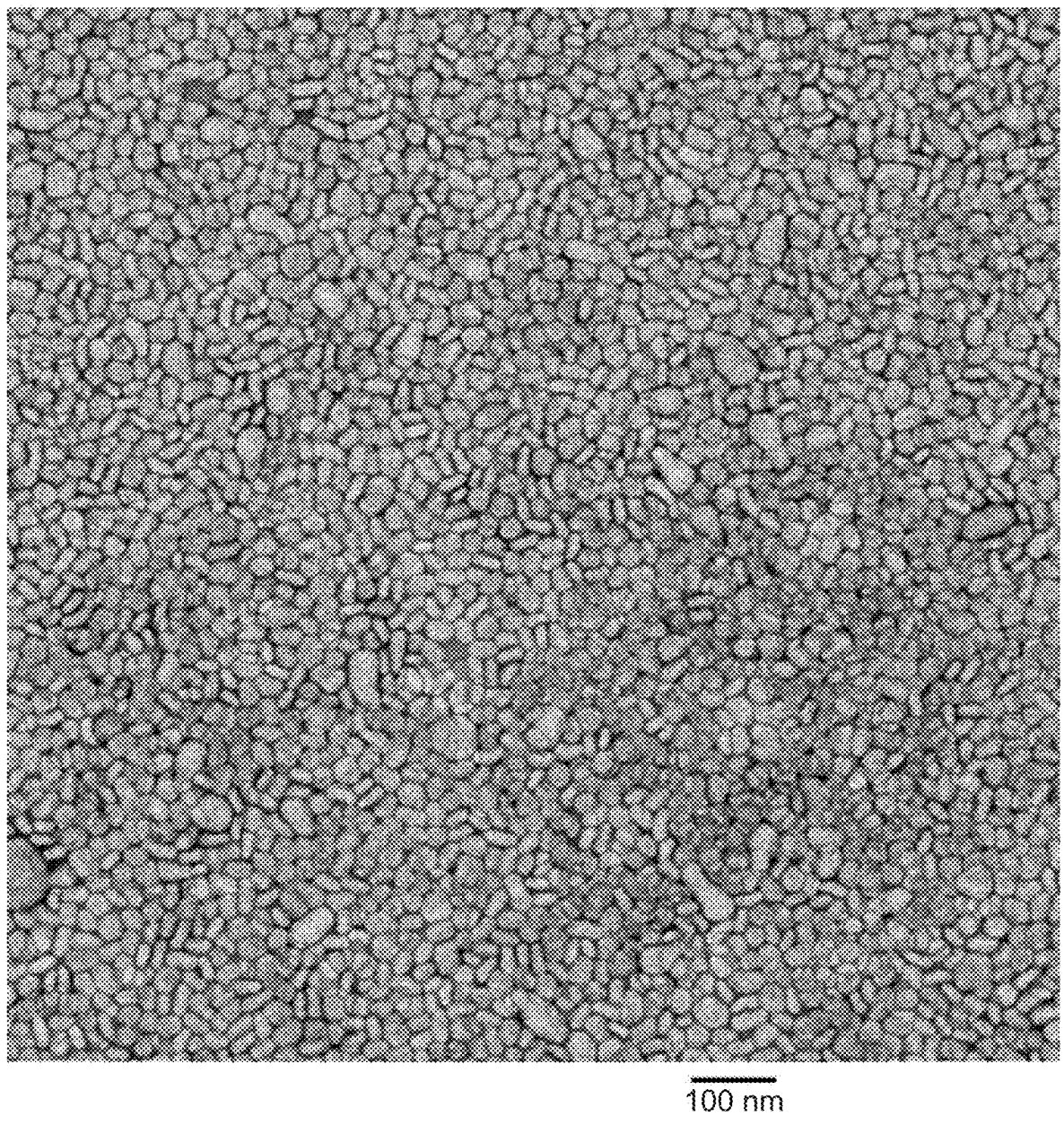
FIG. 2 presents a negative stained TEM image of CPT319C.

Liposomal formulation CPT319C was prepared by loading doxorubicin (DXR) into CPT319B. In a glass bottle 31.4 mg of DXR was dissolved in 30 mL of CPT319B. The mixture was incubated at 42° C. for 4 hours, 99.8% of doxorubicin was encapsulated. The DOCE and DXR dual-loaded liposome was then sterilized by filtration through a 0.22 μm filter. The final composition (% molar) of the CPT317C lipid solution is illustrated in Table 7. The Z-average particle size was 40.7 nm and the molar ratio of DOCE:DXR was 1:1 for CPT319C. The Cryo-TEM images of CPT319C are shown in FIG. 1. The DXR crystals formed inside the liposome can be seen from these images. The negative stained TEM image of CPT319C is shown in FIG. 2, which indicates particle size and homogeneity.

TABLE 7

Lipid Composition of Example 7.

| Component | CPT319C % (molar)* |
|---|---|
| DOPC | 62.8 |
| Cholesterol | 17.8 |
| DC-Cholesterol | 15.4 |
| mPEG2000-DSPE | 4.6 |
| DOCE | 3.5 |
| DXR | 3.5 |

*The value represents the molar % of each component vs. total lipids.

Example 8: Preparation of Liposomal Formulation CPT323C

CPT323C was prepared in the absence of pegylated lipid, thus the pegylated lipid is optional to the formulations. The lipids/DOCE solution was prepared by dissolving 300 mg of DOPC, 50 mg of cholesterol, 70 mg of DC-Cholesterol, and 25 mg of DOCE in 10 mL of anhydrous ethanol. In addition, three aqueous solutions of 250 mM ammonium sulfate, pH 6.5 were used. Ten milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass bottle and was then concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter.

Three milliliters of the DOCE loaded liposome was then mixed with 3 mg of DXR that had been pre-dissolved in the histidine/sucrose buffer at 7 mg/mL, incubated at 42° C. for 6 hours, 96.3% of DXR was encapsulated The DOCE and DXR dual-loaded liposome was then sterilized by filtration through a 0.22 μm filter to obtain CPT323C. The composition (% molar) of the liposomal formulation CPT323C lipid solution is illustrated in Table 8. The Z-average particle size of the dual-loaded liposome was 49.0 nm for CPT323C.

TABLE 8

Lipid Composition of Example 8.

| Component | CPT323C % (molar)* |
|---|---|
| DOPC | 59.5 |
| Cholesterol | 20.1 |
| DC-Cholesterol | 20.3 |
| DOCE | 4.8 |
| DXR | 4.8 |

*The value represents the molar % of each component vs. total lipids.

Example 9: Preparation of Liposomal Formulation CPT324C

Different from other exemplary formulations, CPT324C contains a polyunsaturated lipid-Soy PC and a cationic lipid DOTAP other than DC-cholesterol. The lipids/DOCE solution was prepared by dissolving 60 mg of Soy PC, 40 mg of cholesterol, 60 mg of 1,2-dioleoyl-3-trimethylammonium-propane (chloride salt) (DOTAP), 40 mg of mPEG2000-DSPE, and 25 mg of DOCE in 10 mL of anhydrous ethanol. In addition, three aqueous solutions of 250 mM ammonium sulfate, pH 6.5 were used. Ten milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass bottle and was then concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter.

Three milliliters of the DOCE loaded liposome was then mixed with 0.95 mg of DXR that had been pre-dissolved in the histidine/sucrose buffer at 7 mg/mL, and incubated at 42° C. for 6 hours. The DOCE and DXR dual-loaded liposome was then sterilized by filtration through a 0.22 μm filter to obtain liposomal formulation CPT324C. The composition (% molar) of the CPT324C lipid solution is illustrated in Table 9. The Z-average particle size of the dual-loaded liposome was 56 nm for CPT324C.

TABLE 9

Lipid Composition of Example 9.

| Component | CPT324C % (molar)* |
|---|---|
| Soy PC | 27.6 |
| Cholesterol | 36.9 |
| mPEG2000-DSPE | 4.8 |
| DOTAP | 30.7 |
| DOCE | 11.0 |
| DXR | 11.0 |

*The value represents the molar % of each component vs. total lipids.

Example 10: Preparation of Liposomal Formulation CPT313C

CPT313C was prepared in the presence of DC-cholesterol and the absence of cholesterol. The lipids/DOCE solution was prepared by dissolving 33 mg of Soy PC, 20.5 mg of DC-Cholesterol, 11 mg of mPEG2000-DSPE, and 4.4 mg of DOCE in 2.2 mL of anhydrous ethanol. In addition, three aqueous solutions of 250 mM ammonium sulfate, pH 6.5 were used. 2.2 milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass vial. The buffer was changed into a histidine/sucrose buffer (10 mM histidine, 9.2% sucrose, pH 6.5) by dialysis. The formulation was then sterilized by filtration through a 0.22 μm filter.

Two milliliters of the DOCE loaded liposome was then mixed with 0.5 mg of DXR that had been pre-dissolved in the histidine/sucrose buffer at 10 mg/mL, and incubated at 42° C. for 2 hours, 90.6% of DXR was encapsulated. The encapsulated liposome was then sterilized by filtration through a 0.22 μm filter to obtain liposomal formulation CPT313C. The composition (% molar) of the CPT313C lipid solution is illustrated in Table 10. The Z-average particle size of the dual-loaded liposome was 38.7 nm for CPT313C.

TABLE 10

Lipid Composition of Example 10.

| Component | CPT313C % (molar)* |
|---|---|
| Soy PC | 50.4 |
| mPEG2000-DSPE | 4.4 |
| DC-Cholesterol | 45.2 |
| DOCE | 6.5 |
| DXR | 6.5 |

*The value represents the molar % of each component vs. total lipids.

Example 11: Dual-Loaded Liposome CPT319C Augments Efficacy Against Non-Small Cell Lung Cancer (NSCLC)

Female Balb/c nude mice ranging from 6-8 weeks of age were inoculated subcutaneously on the right flank with NSCLC cell line A549 tumor cells ($1 \times 10^7$ cells/mouse) in 0.1 mL phosphate buffered saline (PBS) buffer for tumor development. On Day 16 following tumor cell inoculation (tumor size was approximately 117 mm$^3$), treatments were started with formulations of CPT319A at 5 mg/kg doxorubicin, CPT319B at 7.5 mg/kg docetaxel, CPT319C at 5 mg/kg doxorubicin/7.5 mg/kg docetaxel, or the non-liposomal combination formulation of 5 mg/kg doxorubicin/7.5 mg/kg docetaxel by intravenous (IV) injection through the tail vein. Three additional treatments were administered on Day 20, Day 27, and Day 34. The study was terminated on Day 45. The tumor growth curves and tumor weight inhibition percentages (TW inh %) on Day 45 of the formulations compared to the PBS control group are shown in FIG. 3.

Figure 3:
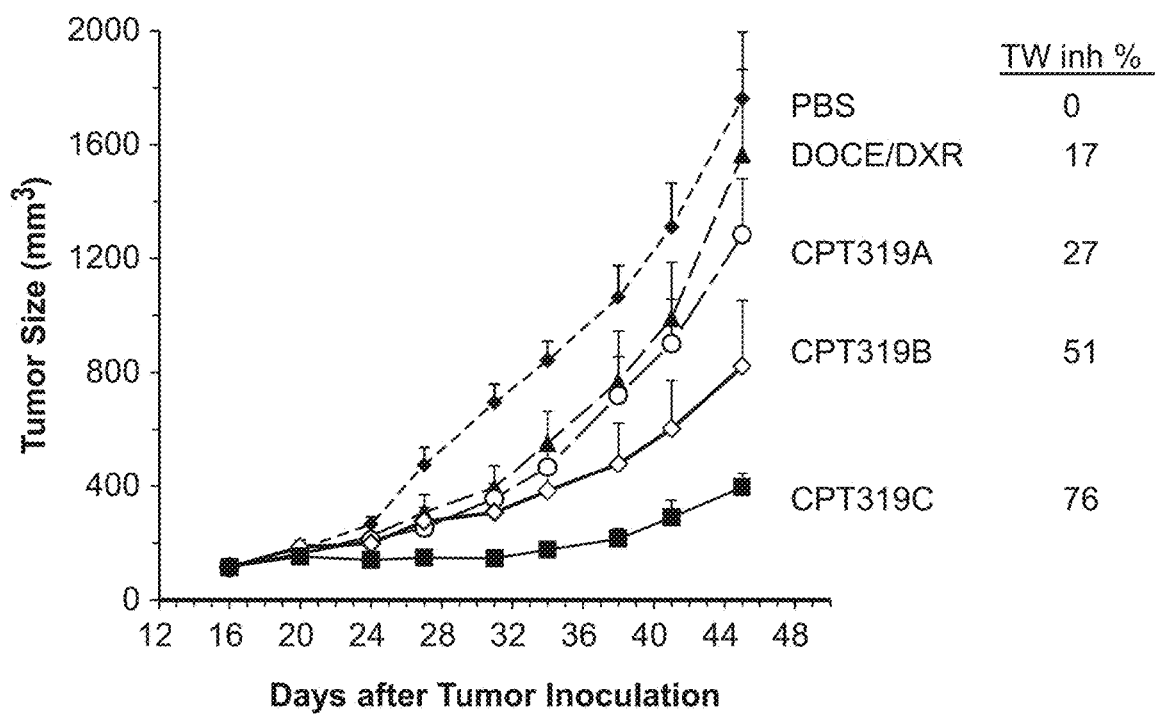
FIG. 3 illustrates NSCLC tumor growth curves and tumor weight inhibition percentages (TW inh %) after administration of liposomal (CPT319A, CPT319B, or CPT319C) or non-liposomal formulations of docetaxel/doxorubicin, compared to a control group.

To summarize, FIG. 3 shows that dual-loaded Liposome CPT319C enhances the antitumor activity of the formulation in NSCLC Xenograft mouse model. All of the liposomal formulations were more efficacious than the non-liposomal combination of DOCE/DXR. In addition, the dual-loaded liposome, CPT319C was the most efficacious formulation in this example. Compared to the PBS control group, CPT319C reduced 76% of the tumor weight that was significantly more efficacious than the 51% of DOCE liposome CPT319B, 27% of DXR liposome CPT319A, and 17% of the non-liposomal combination of DOCE/DXR.

Example 12: Dual-Loaded Liposome CPT307C Augments Efficacy Against Non-Small Cell Lung Cancer (NSCLC)

Female Balb/c nude mice ranging from 6-8 weeks of age were inoculated subcutaneously at the right flank with NSCLC cell line A549 tumor cells ($1 \times 10^7$ cells/mouse) in 0.1 mL PBS buffer for tumor development. On Day 16 following tumor cell inoculation (tumor size was approximately 117 mm$^3$), treatments were started with formulations of CPT307A at 5 mg/kg doxorubicin, CPT307B at 7.5 mg/kg docetaxel, CPT307C at 5 mg/kg doxorubicin/7.5 mg/kg docetaxel, or the non-liposomal combination formulation of 5 mg/kg doxorubicin/7.5 mg/kg docetaxel by intravenous (IV) injection through the tail vein. Three additional treatments were administered on Day 20, Day 27, and Day 34. The study was terminated on Day 45. The tumor growth curves and tumor weight inhibition percentages (TW inh %) on Day 45 of the formulations compared to the PBS control group are shown in FIG. 4.

Figure 4:
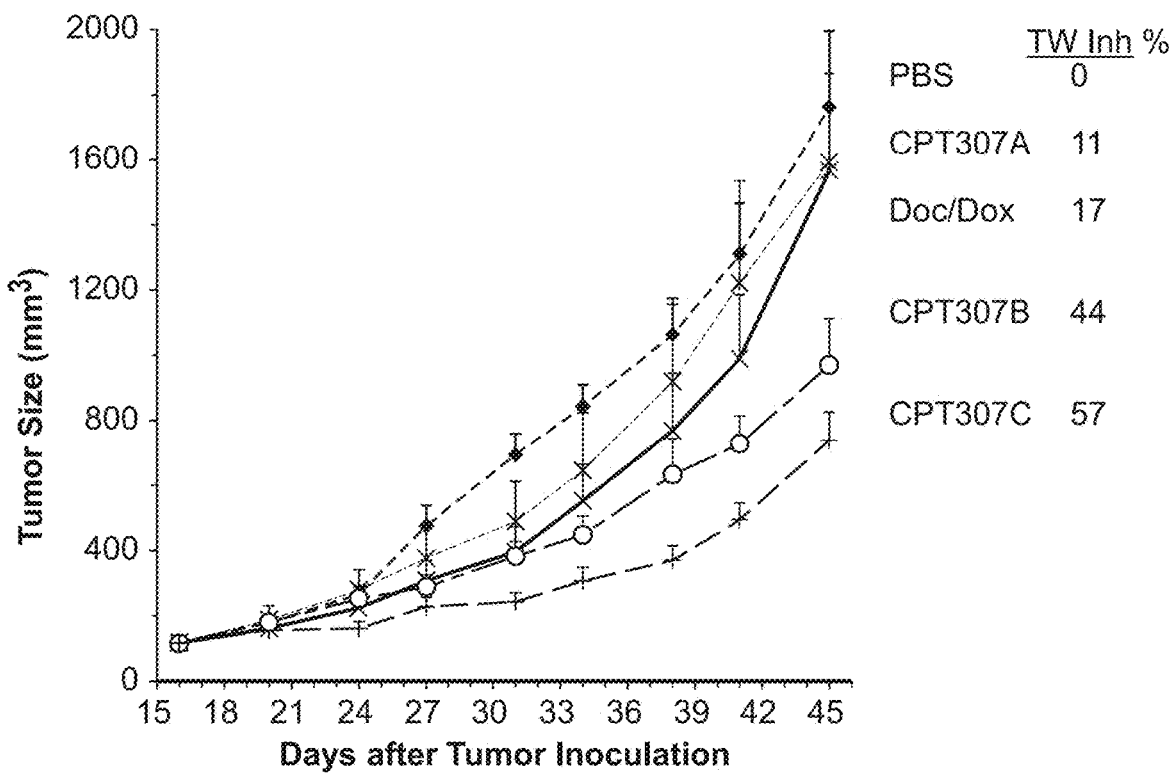
FIG. 4 illustrates NSCLC tumor growth curves and tumor weight inhibition percentages (TW inh %) after administration of liposomal (CPT307A, CPT307B, or CPT307C) or non-liposomal formulations of docetaxel/doxorubicin, compared to the control group.

To summarize, FIG. 4 shows that dual-loaded liposome CPT307C augments efficacy against non-small cell lung cancer (NSCLC). All of the liposomal formulations were more efficacious than the non-liposomal combination of DOCE/DXR. In addition, the dual-loaded liposome, CPT307C was the most efficacious in this example. Compared to the PBS control group, the dual-loaded liposome CPT307C 57% of the tumor weight that is significant more efficacious than the 44% of DOCE liposome CPT307B, 11% of DXR liposome CPT307A, and 17% of the non-liposomal combination of DOCE/DXR.

Figure 5:
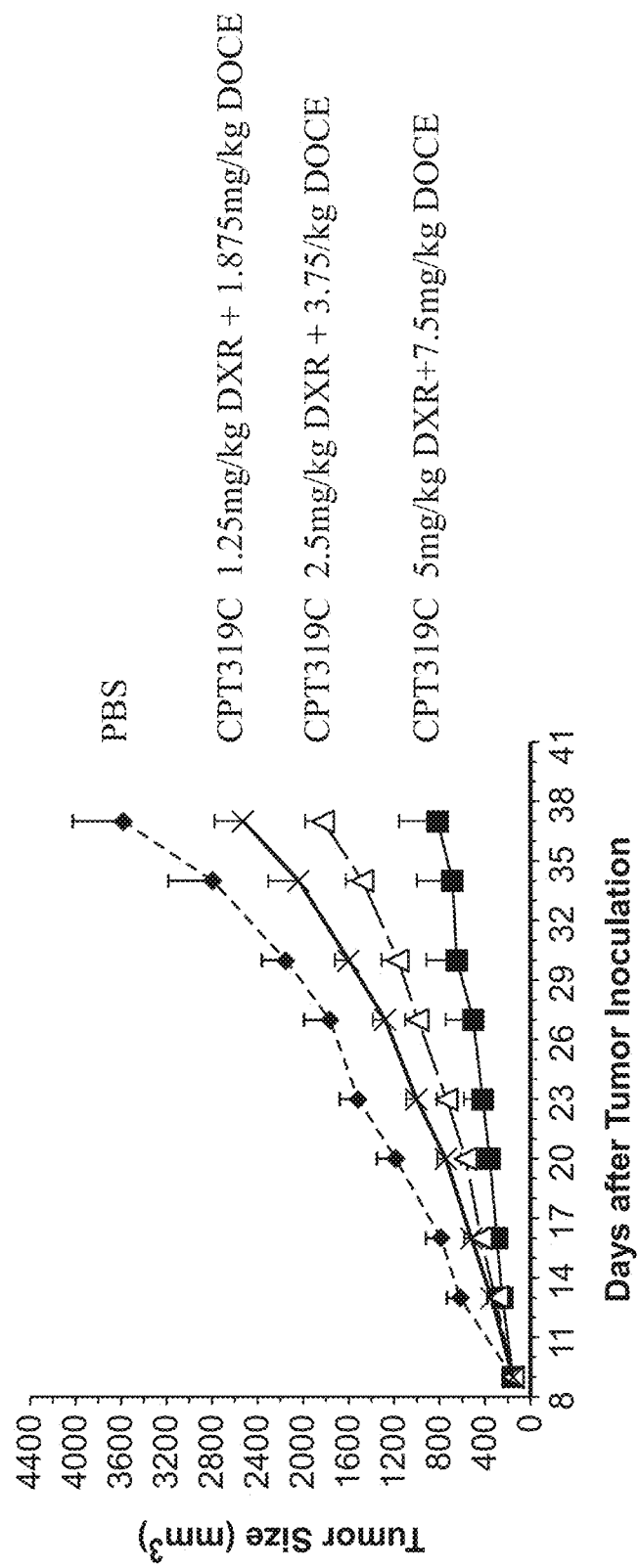
FIG. 5 illustrates colon cancer tumor growth curves after administration of three different doses of liposomal formulation (CPT319C), compared to the control group.

Example 13: Antitumor Activity of Dual-Loaded Liposome CPT319C Against Human Colon Cancer in Xenograft Mouse Model Female Balb/c nude mice ranging from 6-8 weeks of age were inoculated subcutaneously at the right flank with human colon cancer cell line HCT-116 tumor cells ($5 \times 10^6$ cells/mouse) in 0.1 mL PBS buffer for tumor development. On Day 9 following tumor cell inoculation (tumor size was approximately 141 mm$^3$), treatments were started with formulations of CPT319C at 3 different doses: 5 mg/kg doxorubicin/7.5 mg/kg docetaxel, 2.5 mg/kg doxorubicin/3.75 mg/kg docetaxel, or 1.25 mg/kg doxorubicin/1.875 mg/kg docetaxel by intravenous (IV) injection through the tail vein. Two additional treatments were administered on Day 16 and Day 23. The study was terminated on Day 37. The tumor growth curves shown in FIG. 5, which illustrates dose responses of the liposomal formulations in a HCT-116 human colon cancer xenograft model. Compared to the PBS control group, the dual-loaded CPT319C reduced 77% of the HCT-116 tumor size on Day 37 in the 5 mg/kg doxorubicin/7.5 mg/kg docetaxel group, 49% in the group treated with 2.5 mg/kg doxorubicin/3.75 mg/kg docetaxel, and 29% in the group treated with 1.25 mg/kg doxorubicin/1.875 mg/kg docetaxel.

Figure 6:
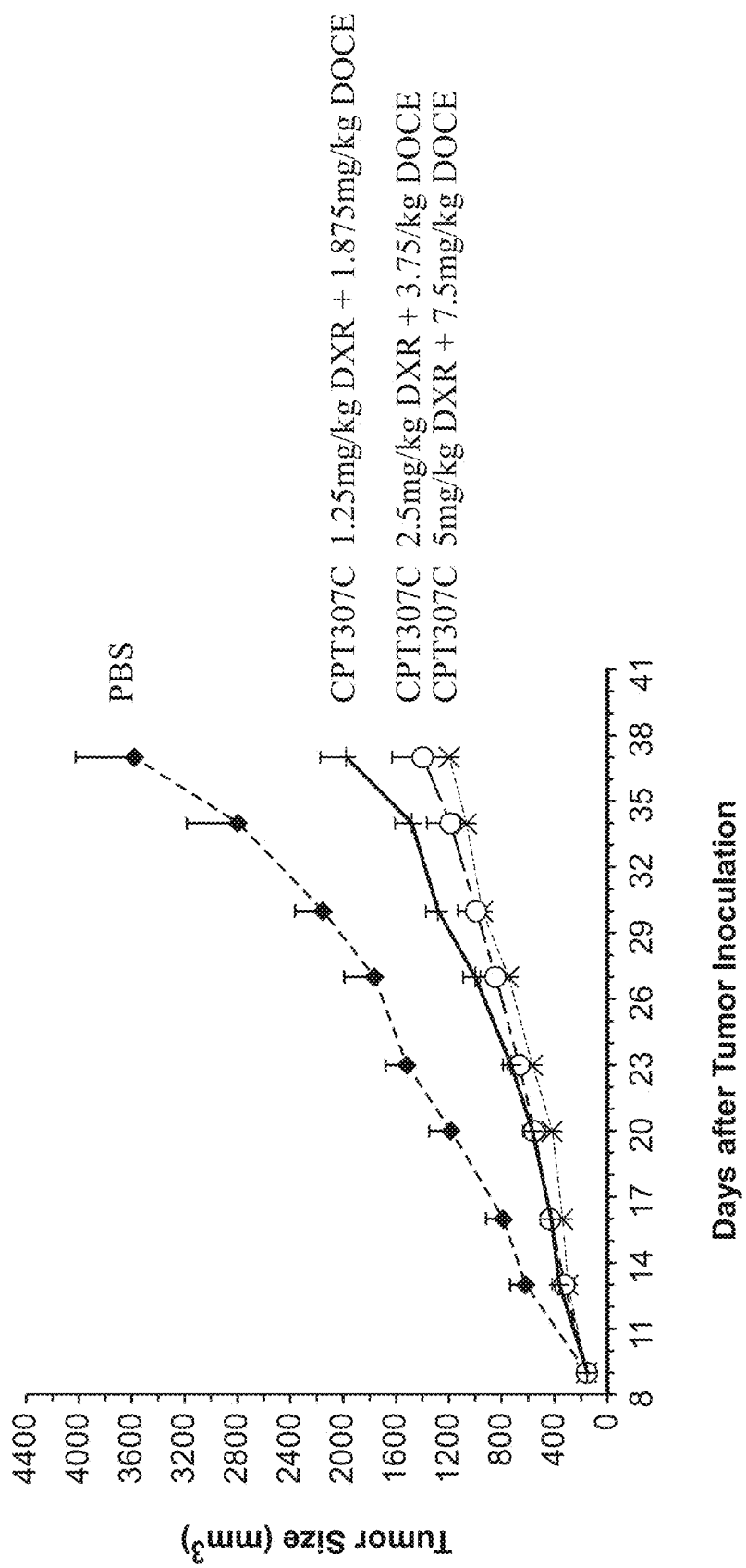
FIG. 6 illustrates colon cancer tumor growth curves after administration of three different doses of liposomal formulation (CPT307C), compared to the control group.

Example 14: Antitumor Activity of Dual-Loaded Liposome CPT307C Against Human Colon Cancer in Xenograft Mouse Model Female Balb/c nude mice ranging from 6-8 weeks of age were inoculated subcutaneously at the right flank with human colon cancer cell line HCT-116 tumor cells ($5 \times 10^6$ cells/mouse) in 0.1 mL PBS buffer for tumor development. On Day 9 following tumor cell inoculation (tumor size was approximately 141 mm$^3$), treatments were started with formulations of CPT307C at 3 different doses: 5 mg/kg doxorubicin/7.5 mg/kg docetaxel, 2.5 mg/kg doxorubicin/3.75 mg/kg docetaxel, or 1.25 mg/kg doxorubicin/1.875 mg/kg docetaxel by intravenous (IV) injection through the tail vein. Two additional treatments were administered on Day 16 and Day 23. The study was terminated on Day 37. The tumor growth curves shown in FIG. 6, which illustrates dose responses of the liposomal formulations in a HCT-116 human colon cancer xenograft model. Compared to the PBS control group, the dual-loaded CPT307C reduced 67% of the HCT-116 tumor size on Day 37 in the 5 mg/kg doxorubicin/7.5 mg/kg docetaxel group, 61% in the group treated with 2.5 mg/kg doxorubicin/3.75 mg/kg docetaxel, and 45% in the group treated with 1.25 mg/kg doxorubicin/1.875 mg/kg docetaxel.

Example 15: Antitumor Activity of Dual-Loaded Liposome CPT319C and CPT307C Against Human Breast Cancer in Xenograft Mouse Model Female Balb/c nude mice ranging from 6-8 weeks of age were inoculated subcutaneously at the right flank with human breast cancer cell line MDA-MB-231 tumor cells (7×10$^6$ cells/mouse) in 0.1 mL PBS buffer for tumor development. On Day 7 after tumor cell inoculation (tumor size was approximately 174 mm$^3$), treatments were started with formulations of CPT319C or CPT307C at 5 mg/kg doxorubicin/7.5 mg/kg docetaxel by intravenous (IV) injection through the tail vein. Two additional treatments were made on Day 14 and Day 21. The study was terminated on Day 31. The tumor growth curves were shown in FIG. 7.

Figure 7:
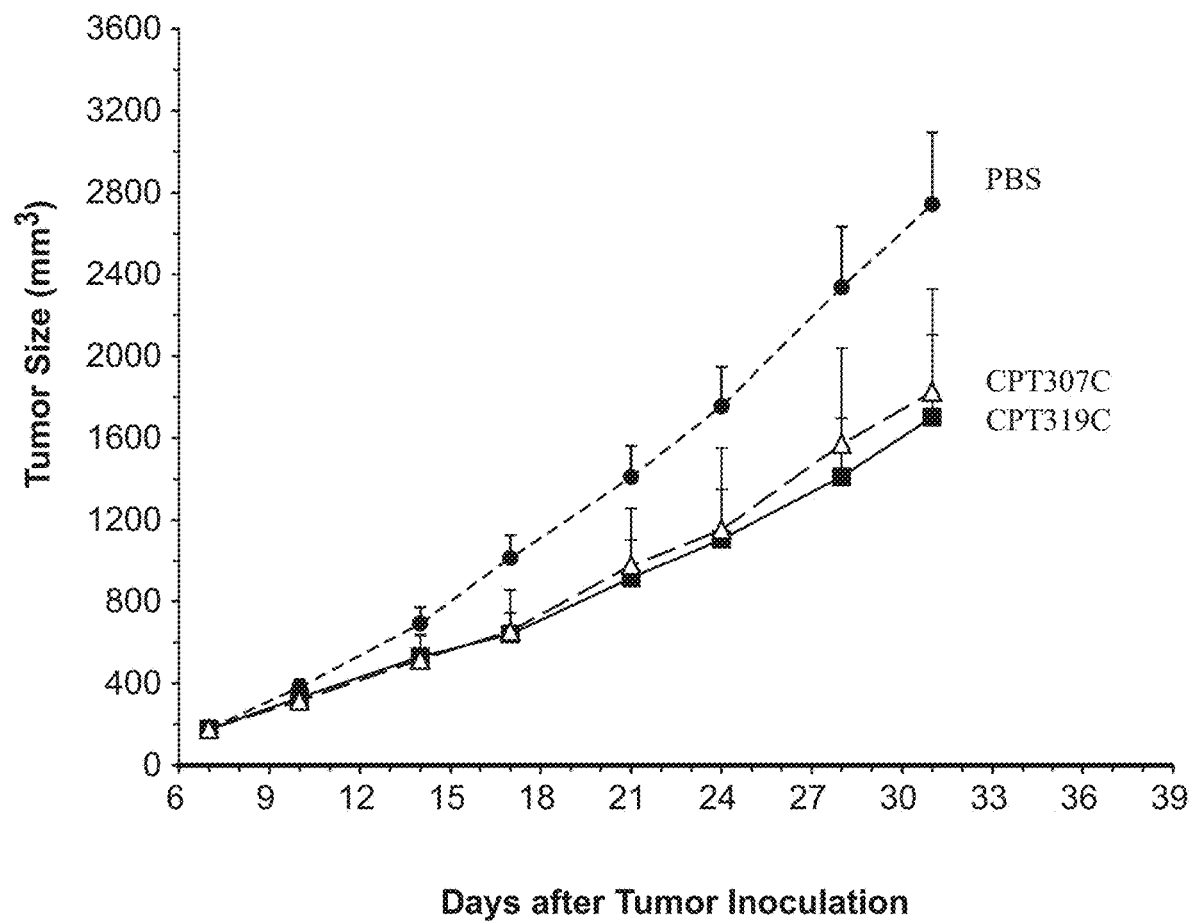
FIG. 7 illustrates breast cancer tumor growth curves on Day 31 after administration of liposomal formulations (CPT307C or CPT319C), compared to the control group.

To summarize, FIG. 7 shows CPT319C and CPT307C antitumor activity in a human breast cancer xenograft model. Compared to the PBS control group, the tumor size was reduced 38% and 32% in the group treated by CPT319C and CPT307C, respectively.

Example 16: Antitumor Activity of Dual-Loaded Liposome CPT319C Against Human Primary Hepatocellular Carcinoma in Xenograft Mouse Model Female Balb/c nude mice ranging from 6-8 weeks were split up into groups of three. Each mouse was inoculated subcutaneously at the right flank with fragments of human primary hepatocellular carcinoma tumor cells (P3 WP HCC) for tumor development. On Day 32 after tumor inoculation (tumor size was approximately 143 mm$^3$), treatments were started with a formulation of CPT319C at 5 mg/kg doxorubicin/7.5 mg/kg docetaxel by intravenous (IV) injection through the tail vein. Two additional treatments were made on Day 39 and Day 46. The study was terminated on Day 63. The tumor growth curves are shown in FIG. 8.

Figure 8:
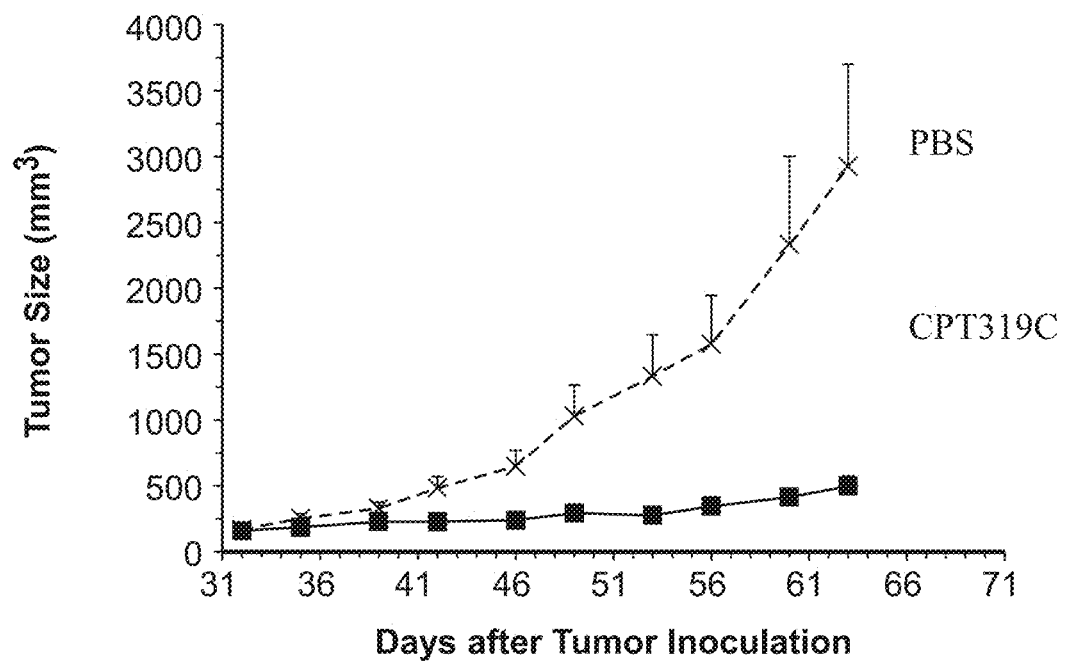
FIG. 8 illustrates hepatocellular carcinoma tumor growth curves after administration of liposomal formulation (CPT319C), compared to the control group.

To summarize, FIG. 8 shows CPT319C antitumor activity in a human primary HCC xenograft model. Tumor growth was almost completely inhibited by CPT319C. Specifically, CPT319C inhibited 88% of tumor growth when the study was terminated on Day 63 compared to the vehicle control group.

Example 17: Cationic Lipid DC-Cholesterol Enhances the Antitumor Activity of Liposomes Against NSCLC Female Balb/c nude mice ranging from 6-8 weeks of age were inoculated subcutaneously at the right flank with NSCLC cell line A549 tumor cells (1×10$^7$ cells/mouse) in 0.1 mL PBS buffer for tumor development. On Day 16 following tumor cell inoculation (tumor size was approximately 117 mm$^3$), treatments were started with formulations of CPT307A or CPT319A at 5 mg/kg doxorubicin, CPT307B or CPT319B at 7.5 mg/kg docetaxel, CPT307C or CPT319C at 5 mg/kg doxorubicin/7.5 mg/kg docetaxel, or the non-liposomal combination formulation of 5 mg/kg doxorubicin/7.5 mg/kg docetaxel by intravenous (IV) injection through the tail vein. Three additional treatments were made on Day 20, Day 27, and Day 34. The study was terminated on Day 45. The lipid compositions of the CPT307 (without DC-Cholesterol) and CPT319 (with DC-Cholesterol) formulations are shown in Table 11. The tumor growth curves are shown in FIG. 9.

Figure 9:
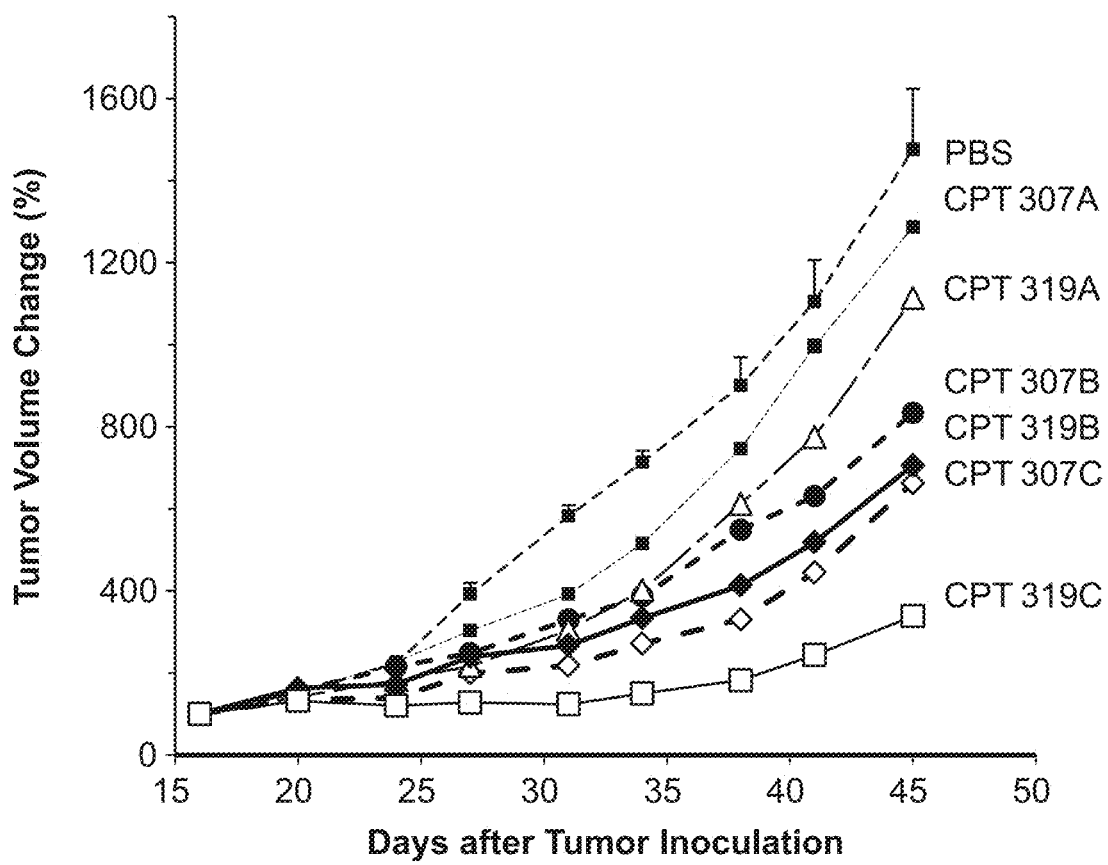
FIG. 9 illustrates NSCLC tumor growth curves after administration of liposomal formulations (CPT307A-C or CPT319A-C), compared to the control group.

To summarize, FIG. 9 shows that a cationic lipid DC-cholesterol can enhance the antitumor activity of the liposomes against NSCLC. The tumor inhibition rank order (from low to high) was: PBS<CPT307A<CPT319A<CPT307B<CPT319B<CPT307C<CPT319C. For each instance, CPT319 (with DC-Cholesterol) was no exceptionally more efficacious than CPT307 (without DC-Cholesterol) indicating that the incorporation of the cationic lipid DC-cholesterol enhances the anti-tumor efficiency of the liposomal formulations.

TABLE 11

Lipid Compositions of Example 17.

| Formulation | DC-cholesterol | cholesterol | mPEG-DSPE | DOPC |
|---|---|---|---|---|
| CPT319 | 15 | 18 | 5 | 62 |
| CPT307 | 0 | 24 | 6 | 70 |

Example 18: Cationic Lipid DC-Cholesterol Enhances the Antitumor Activity of Liposomes Against Colon Cancer Female Balb/c nude mice ranging from 6-8 weeks of age were inoculated subcutaneously at the right flank with human colon cancer cell line HCT-116 tumor cells (5×10$^6$ cells/mouse) in 0.1 mL PBS buffer for tumor development. On day 9 following tumor cell inoculation (tumor size was approximately 141 mm$^3$), treatments were started with formulations of CPT319C (containing DC-Cholesterol) or CPT307C (without DC-Cholesterol) at 5 mg/kg DXR/7.5 mg/kg DOCE by intravenous (IV) injection through the tail vein. Two additional treatments were made on Day 16 and Day 23. The study was terminated on Day 37. The tumor growth curves and tumor weight inhibition percentages (TW Inh %) on Day 37 of the formulations compared to the vehicle control group are shown in FIG. 10.

Figure 10:
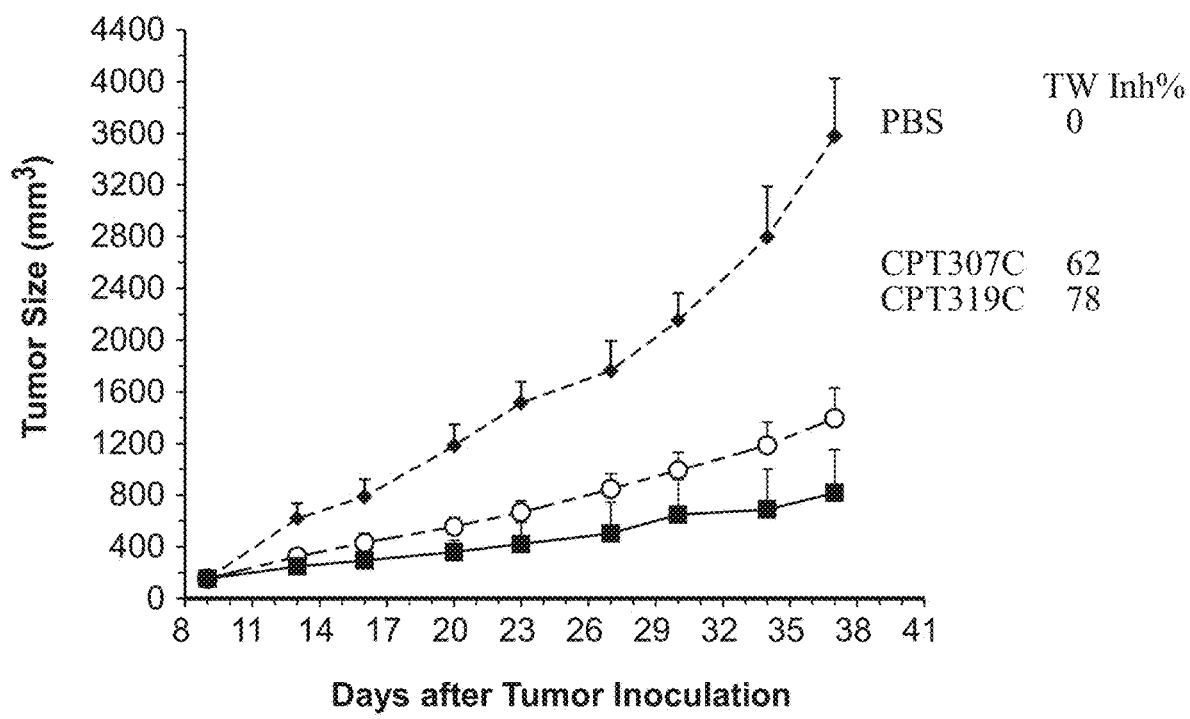
FIG. 10 illustrates colon cancer tumor growth curves and tumor weight inhibition percentages (TW Inh %) after administration of liposomal formulations (CPT307C or CPT219C), compared to the control group.

To summarize, FIG. 10 shows that a cationic lipid DC-cholesterol can enhance the antitumor activity of the liposomes against colon cancer. CPT319C (with DC-Cholesterol) was more efficacious than CPT307C (without DC-Cholesterol), indicating that the incorporation of the cationic lipid DC-cholesterol enhances the anti-tumor efficiency of the liposomal formulations.

Example 19: Liposome Improves Pharmacokinetics (PK) and Cationic Lipid DC-Cholesterol Increases the Half-Life ($t_{1/2}$) of DXR Male CD-1 mice ranging from 20-25 g body weight were split up into groups of three. Each mouse was administered with a single dose of CPT319C or CPT307C at 5 mg/kg DXR/7.5 mg/kg DOCE by intravenous (IV) injection through the tail vein. A non-liposomal combination of DXR/DOCE was used as the control. Blood samples were collected at 0.167, 1, 3, 8, 24, and 48 h after the injection. DXR plasma concentration was determined by liquid chromatography-tandem mass spectrometry. The plasma concentration curves of DXR are shown in FIG. 11.

Figure 11:
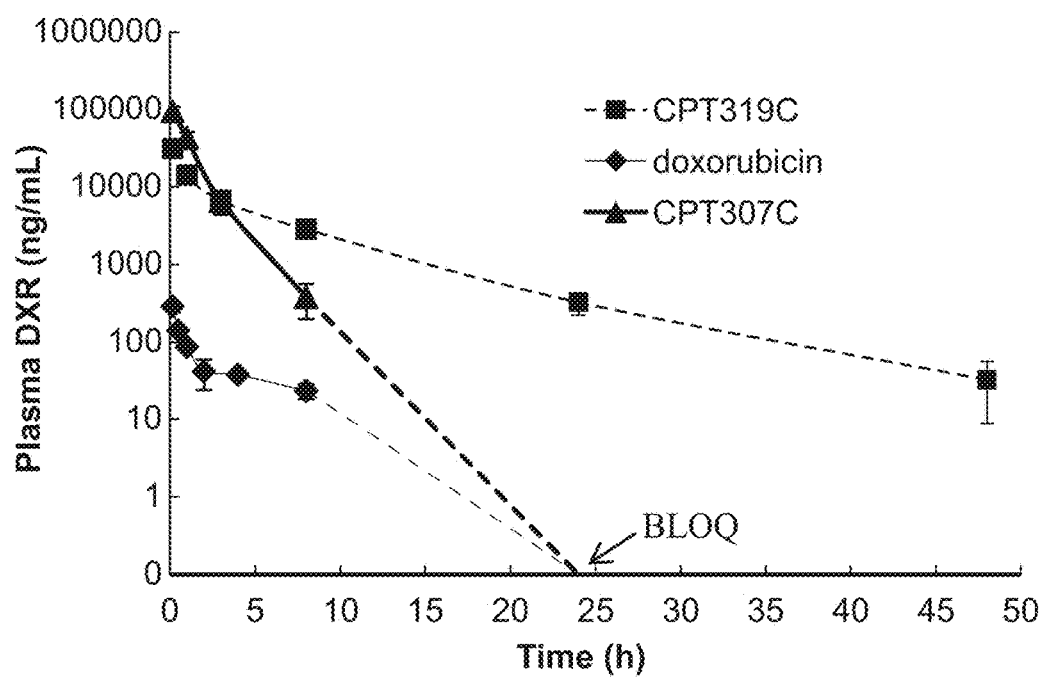
FIG. 11 illustrates plasma concentration curves of doxorubicin after administration of liposomal formulations (CPT319C or CPT307C), compared to non-liposomal formulation of docetaxel/doxorubicin.

To summarize, FIG. 11 shows that a liposome can improve pharmacokinetics and that a cationic lipid DC-cholesterol increases the half-life ($t_{1/2}$) of DXR. BLOQ=Below Limit of Quantitation. The $t_{1/2}$ and area under the plasma concentration time curve (AUC) are provided in the table below. The non-liposomal DXR was cleared quickly from the blood and resulted in a very low AUC (688 h×ng/mL), whereas CPT319C and CPT307C increased AUC by 143 and 204 fold, respectively. Moreover, CPT319C exhibited a 5.9 h $t_{1/2}$ compared to the 1 h $t_{1/2}$ of CPT307C, indicating that the cationic lipid DC-Cholesterol in CPT319C improves PK of the formulation by increasing circulation time in the blood.

TABLE 12 t₁/₂ and AUC of DXR in CD-1 mice

| Formulation | $t_{1/2}$ (h) | AUC (h*ng/mL) |
| --- | --- | --- |
| CPT309C | 5.9 | 98628 |
| CPT307C | 1.0 | 140398 |
| Naked Dox |  | 688 |

The invention claimed is:

1. A pharmaceutical formulation for treating cancer comprising liposomes, the liposomes comprising:
   an active pharmaceutical ingredient (API) comprising docetaxel and doxorubicin;
   a lipid layer comprising an unsaturated phospholipid and a cholesterol; and
   an aqueous interior;
   wherein the docetaxel is in the lipid layer and the doxorubicin is crystallized in the aqueous interior of the liposomes, wherein the lipid layer further comprises a pegylated phospholipid, and wherein the Z-average particle size of the liposomes is about 20-120 nm, and wherein the pharmaceutical formulation provides an antitumor effect in a subject when the pharmaceutical formulation is administered to the subject to less than about 5 mg/kg/week of doxorubicin and less than about 7.5 mg/kg/week of docetaxel to the subject.

2. The pharmaceutical formulation of claim 1, wherein the lipid layer consists essentially of the unsaturated phospholipid, cholesterol, and a pegylated phospholipid.

3. The pharmaceutical formulation of claim 1, wherein the API consists essentially of docetaxel and doxorubicin.

4. The pharmaceutical formulation of claim 1, wherein the lipid layer comprises:
   about 20-75 molar % unsaturated phospholipid;
   about 10-60 molar % cholesterol; and
   about 0-20 molar % pegylated phospholipid.

5. The pharmaceutical formulation of claim 1, wherein:
   the molar ratio of the lipid layer components:doxorubicin is about 100:1 to about 2:1; and
   the molar ratio of the lipid layer components:docetaxel is about 100:1 to about 2:1.

6. The pharmaceutical formulation of claim 1, wherein the molar ratio of doxorubicin:docetaxel is about 10:1 to 1:10.

7. The pharmaceutical formulation of claim 1, wherein the unsaturated phospholipid comprises a polyunsaturated phospholipid or a monounsaturated phospholipid.

8. The pharmaceutical formulation of claim 1, wherein the cholesterol comprises a cationic cholesterol derivative.

9. The pharmaceutical formulation of claim 1, comprised in a pharmaceutical composition comprising a plurality of liposomes.

10. The pharmaceutical formulation of claim 9, wherein the plurality of liposomes are comprised in an intravenous formulation.

11. The pharmaceutical formulation of claim 9, wherein, upon intravenous administration to a subject, at least about 10% of the composition is delivered to the liver.

12. A method comprising administering the pharmaceutical formulation of claim 1 to a subject once every 4 days to 21 days.

13. The method of claim 12, wherein the subject has a cancer.

14. The method of claim 13, wherein the cancer is a lung cancer, colon cancer, breast cancer, stomach cancer, esophagus cancer, prostate cancer, leukemia, head and neck cancer, pancreatic cancer, multiple myeloma, or liver cancer.

15. The pharmaceutical formulation of claim 1, wherein the pegylated phospholipid comprises a 1,2-distearoyl-sn-glycero-3-phosphoethanolamine (DSPE) and wherein the phospholipid is pegylated by PEG 2000.

16. A pharmaceutical formulation for treating cancer comprising liposomes, the liposomes comprising:
   an active pharmaceutical ingredient (API) comprising docetaxel and doxorubicin;
   a lipid layer comprising an unsaturated phospholipid and DC Cholesterol; and
   an aqueous interior;
   wherein the docetaxel is in the lipid layer and the doxorubicin is crystallized in the aqueous interior of the liposomes, wherein the lipid layer further comprises a pegylated phospholipid, and wherein the Z-average particle size of the liposomes is about 20-120 nm, and wherein the pharmaceutical formulation provides an antitumor effect in a subject when the pharmaceutical formulation is administered to the subject to provide less than about 5 mg/kg/week of doxorubicin and less than about 7.5 mg/kg/week of docetaxel to the subject.

17. The pharmaceutical formulation of claim 16, wherein the lipid layer further comprises a cationic lipid.

18. The method of claim 12, wherein the pharmaceutical formulation is administered to the subject once every 4-7 days.

19. The method of claim 12, wherein the pharmaceutical formulation is administered to the subject over the period of 3 weeks to 18 weeks.

20. The method of claim 12, wherein the pharmaceutical formulation is administered to the subject once every 7-21 days.

* * * * *